United States Patent [19]
Shioda et al.

[11] Patent Number: 6,081,371
[45] Date of Patent: Jun. 27, 2000

[54] SURGICAL MICROSCOPE INCLUDING A FIRST IMAGE AND A CHANGING PROJECTION POSITION OF A SECOND IMAGE

[75] Inventors: Keiji Shioda, Tama; Masakazu Mizoguchi, Sagamikomachi; Junichi Nozawa, Hachioji; Takashi Fukaya, Sagamihara, all of Japan

[73] Assignee: Olympus Optical Co., Ltd., Tokyo, Japan

[21] Appl. No.: 09/203,635

[22] Filed: Dec. 1, 1998

[30]     Foreign Application Priority Data

| Jan. 6, 1998 | [JP] | Japan | 10-000895 |
| Sep. 9, 1998 | [JP] | Japan | 10-255557 |
| Oct. 26, 1998 | [JP] | Japan | 10-303778 |

[51] Int. Cl.[7] .......................... G02B 21/18; G02B 21/36; G02B 27/10
[52] U.S. Cl. .......................... 359/372; 359/369; 359/630
[58] Field of Search .......................... 359/368, 369, 359/372, 374–377, 363, 630

[56]           References Cited

U.S. PATENT DOCUMENTS 5,095,887   3/1992   Leon et al. .......................... 606/4
5,453,829   9/1995   Remer et al. .......................... 359/381

FOREIGN PATENT DOCUMENTS

| 62-166310 | 7/1987 | Japan . |
| 63-167317 | 7/1988 | Japan . |
| 3-105305 | 5/1991 | Japan . |
| 8-140991 | 6/1996 | Japan . |

*Primary Examiner*—Jon Henry
*Attorney, Agent, or Firm*—Frishauf, Holtz, Goodman, Langer & Chick, P.C.

[57]                ABSTRACT

A surgical microscope includes an illumination optical system for illuminating a microscope visual field, an observation optical system which has an eyepiece lens and an imaging lens and allows observation of a first image of an observation target by guiding reflected light from the observation target irradiated with illumination light to the eyepiece lens from the illumination optical system, an image projection optical system for projecting a second image as image information within a portion of the microscope visual field, and visual field adjusting mechanism which has a field stop placed at an imaging position of the imaging lens and having a changeable stop shape and adjusts an area of the microscope visual field by changing the stop shape of the field stop in accordance with a projection state of the second image with respect to the microscope visual field.

19 Claims, 17 Drawing Sheets

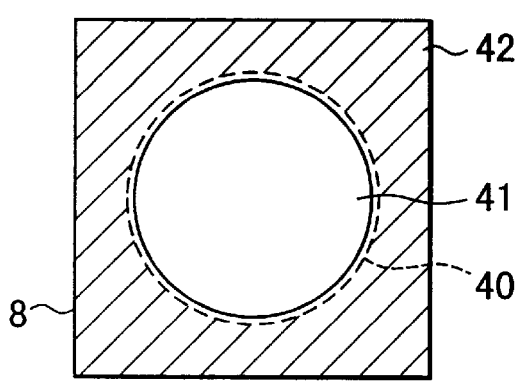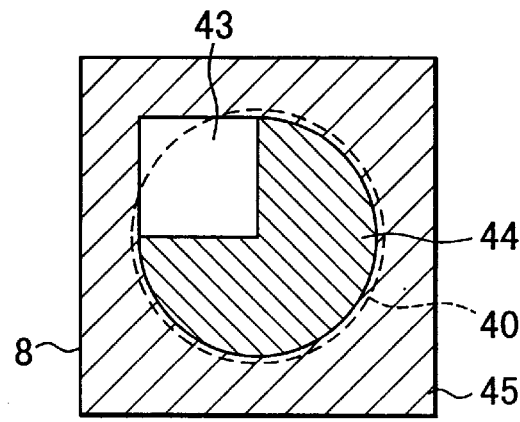
FIG. 3A  FIG. 3B
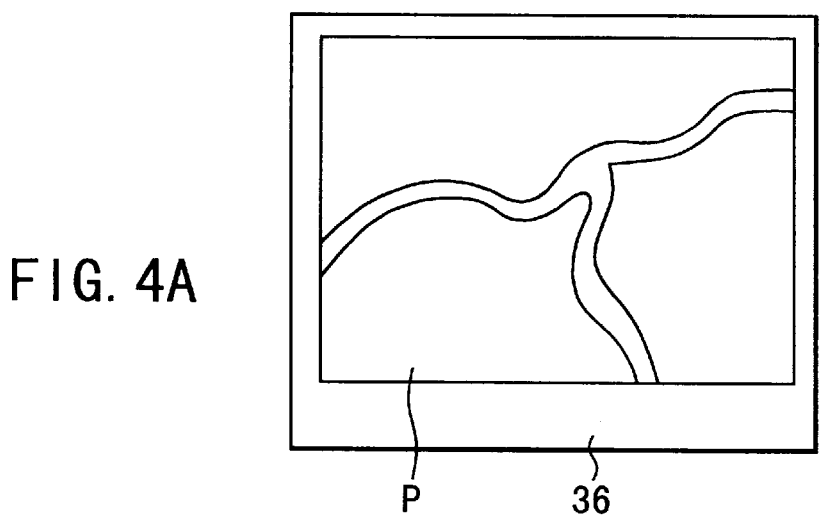
FIG. 4A
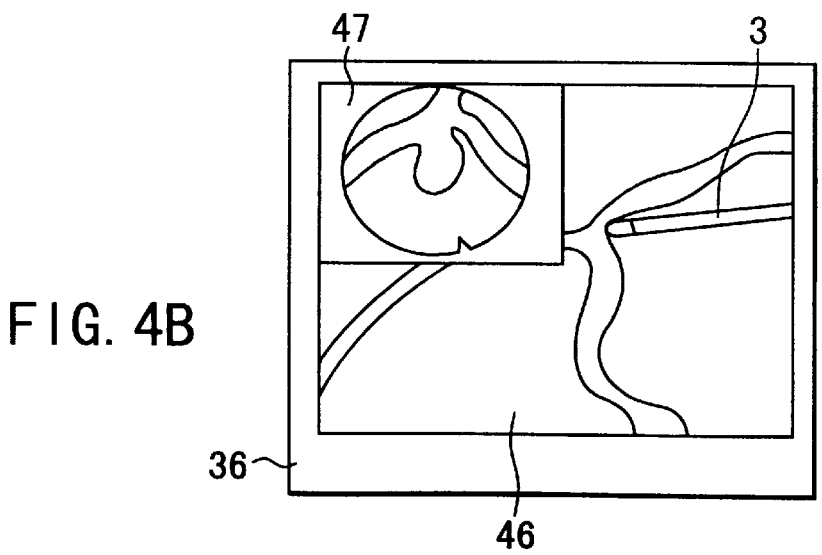
FIG. 4B

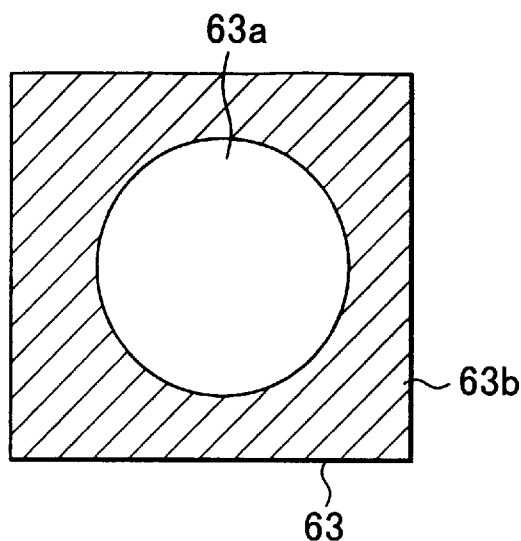 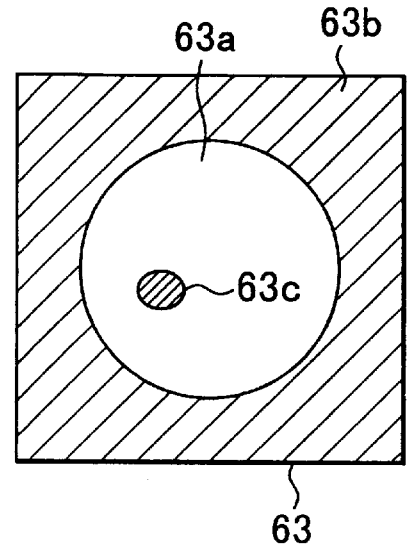
FIG. 11A   FIG. 11B
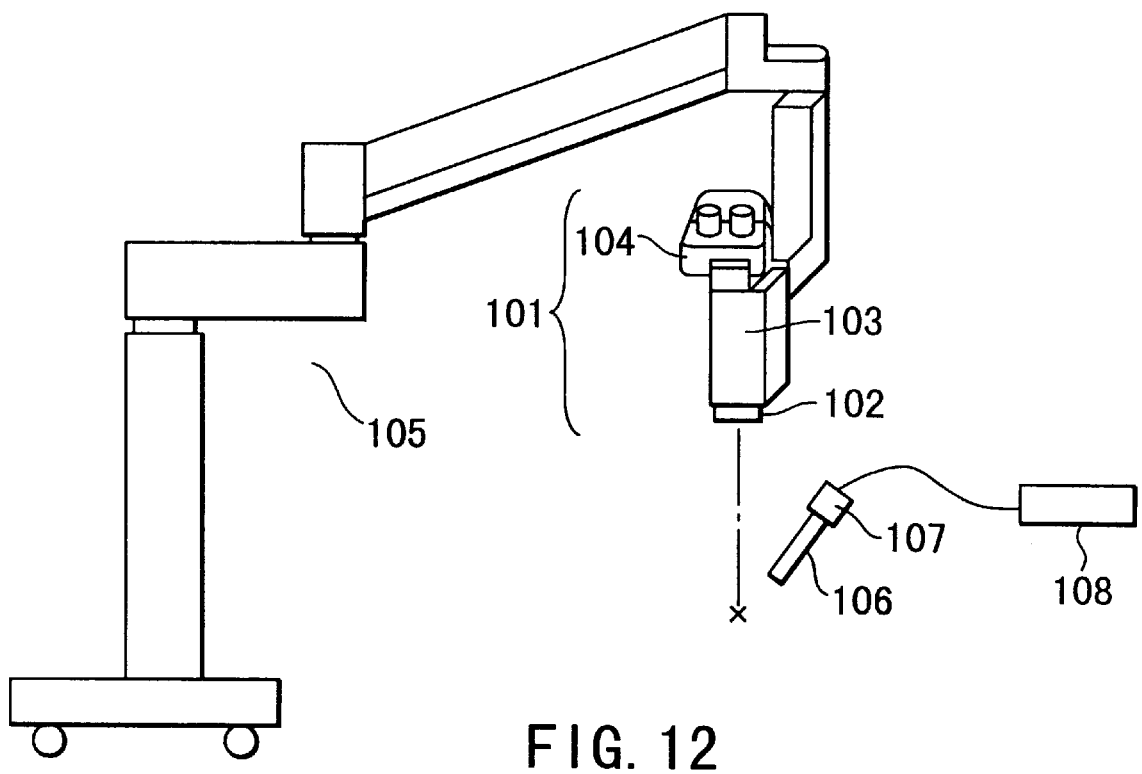
FIG. 12

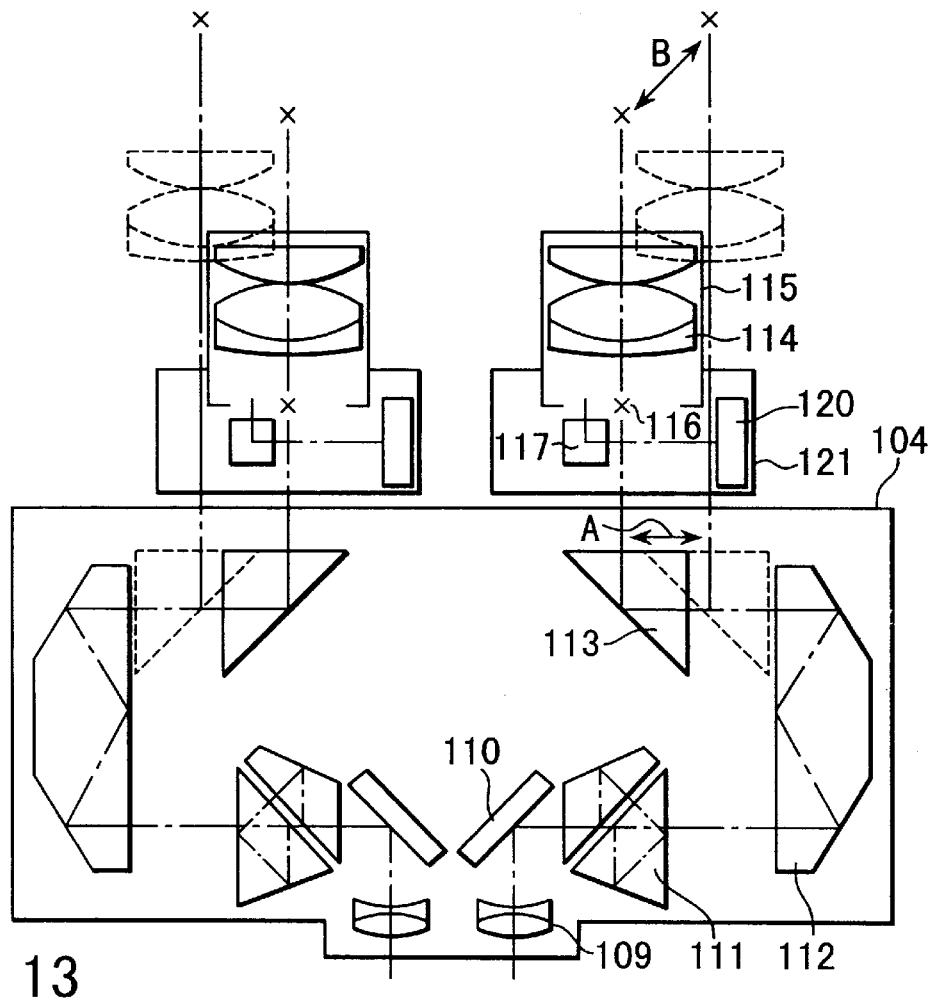
FIG. 13
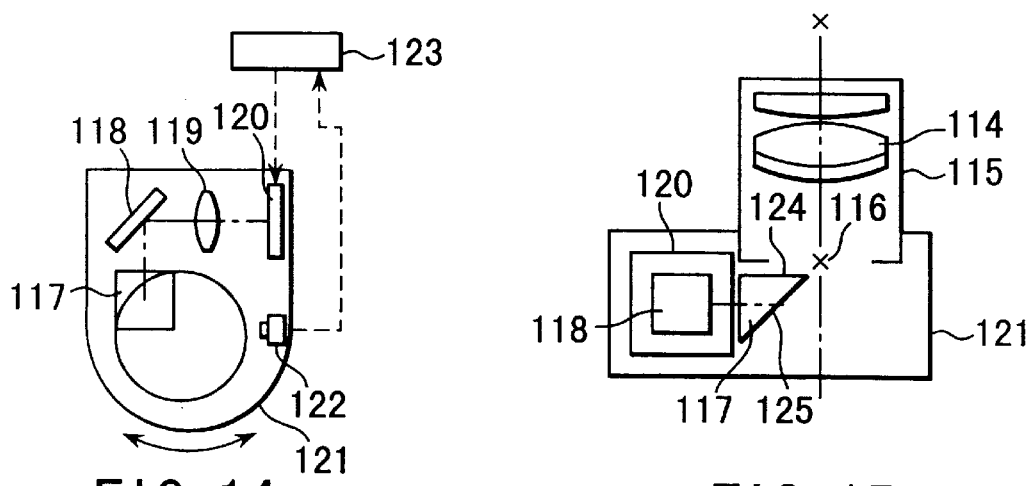
FIG. 14
FIG. 15

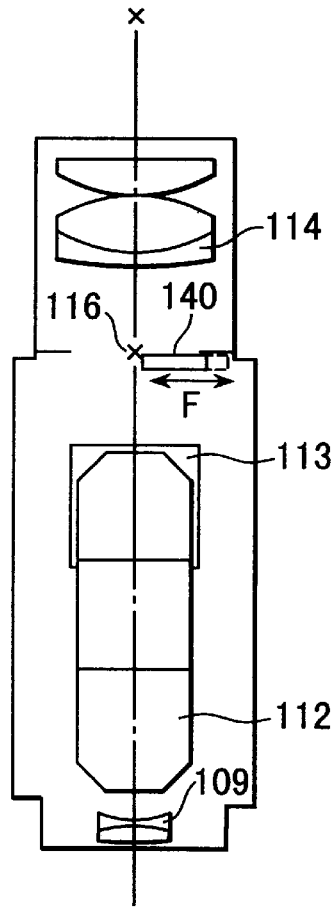
FIG. 28
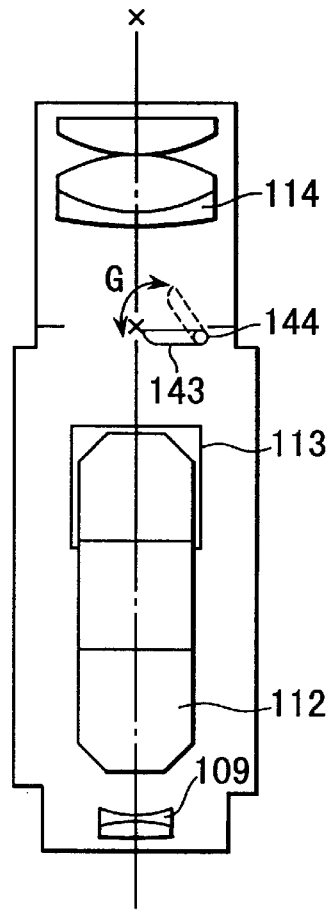
FIG. 29
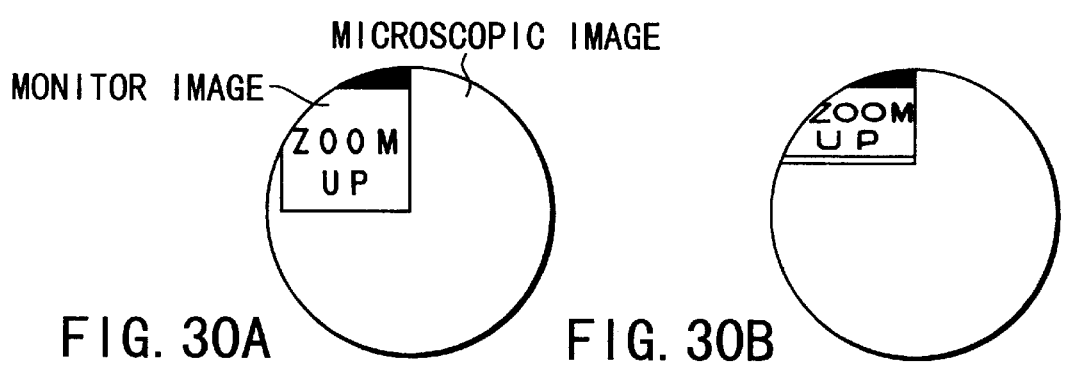
FIG. 30A
FIG. 30B
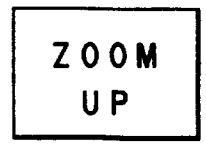
FIG. 31A
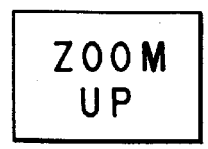
FIG. 31B

SURGICAL MICROSCOPE INCLUDING A FIRST IMAGE AND A CHANGING PROJECTION POSITION OF A SECOND IMAGE

BACKGROUND OF THE INVENTION

The present invention relates to a surgical microscope used in the medical field.

In general, surgical microscopes are used for surgical operations in cerebral surgery, otolaryngology, ophthalmology, and the like, and play an important role, i.e., improving the efficiency of surgical operations by allowing observation of regions under magnification. In addition, in recent years, to perform surgical operations more reliably, endoscopic observation is also performed in conventional surgical operations which have been performed under observation with surgical microscopes. Demands have therefore arisen for techniques of allowing an operator to simultaneously observe a surgical microscopic observation image and an endoscopic observation image within the visual field of a surgical microscope. Demands have also arisen for simultaneous observation of information such as a CT or MRI image before a surgical operation and nerve monitor information during the operation as well as an endoscopic observation image.

In order to meet such demands, a technique of allowing an operator to simultaneously perform observation with a microscope and observation with a second observation means within the visual field of the microscope is disclosed in Jpn. Pat. Appln. KOKAI Publication No. 62-166310. That is, a means for simultaneously guiding an optical image from a stereoscope and a monitor image from an endoscope to the same eyepiece optical system and displaying the sensed images such as an endoscopic image on the eyepiece portion of the stereoscope is disclosed.

A means for displaying data on the eyepiece portion of a stereoscope or the like is disclosed in Jpn. Pat. Appln. KOKAI Publication No. 63-167317. More specifically, a technique of projecting the exit pupil of a data image on a portion outside the exit pupil of a microscopic image by applying a light beam such as data light from the outside of a main observation light beam such as a microscope light beam is disclosed.

In addition, a technique of realizing simultaneous observation with a microscope and an endoscope is disclosed in Jpn. Pat. Appln. KOKAI Publication No. 3-105305. More specifically, a means for projecting the optical image or electronic image obtained by a 2D endoscope onto the eyepiece portion of a stereoscope, a means for guiding a 2D endoscopic image to the right and left optical paths of the microscope, and a member for shielding a microscope light beam are disclosed.

A means for displaying an endoscopic image or the vital data of a patient within or near the visual field of a microscope is disclosed in Jpn. Pat. Appln. KOKAI Publication No. 8-140991. More specifically, a technique of guiding an endoscopic image or the like into the visual filed of a microscope through a half mirror, a technique of displaying a microscopic image and an endoscopic image within the same visual field by guiding a microscope optical path and an endoscope optical path to an eyepiece lens in a parallel state (see FIG. 3 in this reference), and the like are disclosed.

According to the technique disclosed in Jpn. Pat. Appln. KOKAI Publication No. 62-166310, however, when the image obtained by the monitor optical system is to be observed outside the optical image obtained by the microscope optical system, since the field stop of the microscope interferes with the observation, the monitor image is vignetted or the field stop of the microscope must be removed. Assume that the field stop of the microscope is removed. In this case, when only the microscopic image is to be observed, since no field stop is placed in the area where the monitor image is to be projected, even an image outside the image circle formed by the microscope optical system can be seen. For this reason, the operator must always observe even a peripheral image with poor image quality, and hence suffers from unnecessary fatigue as the image quality deteriorates. According to the technique disclosed in Jpn. Pat. Appln. KOKAI Publication No. 62-166310, part of the visual field of the microscope is shielded by the reflecting member placed near the imaging plane of the microscope. For this reason, when this shielded portion is to be observed, the overall microscope must be moved to move the observation point out of the shielded portion of the visual field of the microscope. The movement of the overall microscope interrupts a surgical operation and reduces the operation efficiency. In addition, in this reference, the positional relationship between the imaging plane of the microscope and the reflecting member is not clarified. When, therefore, the center of the reflecting member is positioned on the imaging plane of the microscope as shown in the drawing, the upper and lower portions of the reflecting member are separated from the imaging plane of the microscope to cause defocusing. As a result, the boundary between the visual field of the microscope and the image (the image obtained by the second observation means and put in the visual field of the microscope by the reflecting member) cannot be clearly discriminated.

According to the technique disclosed in Jpn. Pat. Appln. KOKAI Publication No. 3-105305, since a microscopic image and an endoscopic image are superimposed on each other within the same visual field (the microscopic image and the endoscopic image are coupled to each other by the half mirror), each image cannot be observed in detail unless one of the image light beams is shielded. It is therefore difficult to simultaneously observe a microscopic image and an endoscopic image within the visual field of the microscope while orientating the endoscope. In addition, since the endoscopic image is always superimposed on the entire microscopic image, the operator cannot concentrate on operation under the microscope.

Furthermore, as disclosed in Jpn. Pat. Appln. KOKAI Publication No. 8-140991, according to the technique of guiding the microscope optical path and the endoscope optical path to the eyepiece lens in a parallel state, since the endoscope optical path is positioned outside the microscope optical path and cannot be inserted/withdrawn into/from the microscope body, no field stop is formed at a portion corresponding to the endoscope optical path even if endoscopic observation is not required. For this reason, as in the technique disclosed in Jpn. Pat. Appln. KOKAI Publication No. 62-166310, an image outside the image circle of the microscope optical system can be seen.

When an endoscopic image is to be observed, it is required that a monitor image be observed while the image is enlarged to the maximum size to be easily seen. In this case, however, since the microscopic image inevitably decreases in size, this technique is not so practical.

BRIEF SUMMARY OF THE INVENTION

It is an object of the present invention to provide a surgical microscope which allows an operator to properly observe a microscopic optical image and a monitor image from an image projection optical system within the same visual field, and forms a clear boundary between a microscopic image and a monitor image to allow the operator reliably discriminate the two images.

The object of present invention can be achieved by the following surgical microscope. According to the present invention, there is provided a surgical microscope comprising an illumination optical system for illuminating a microscope visual field, an observation optical system which has an eyepiece lens and an imaging lens and allows observation of a first image of an observation target by guiding reflected light to the eyepiece lens from the observation target irradiated with illumination light from the illumination optical system, an image projection optical system for projecting a second image as image information within a portion of the microscope visual field, and visual field adjusting mechanism which has a field stop placed at an imaging position of the imaging lens and having a changeable stop shape and adjusts an area of the microscope visual field by changing the stop shape of the field stop in accordance with a projection state of the second image with respect to the microscope visual field.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 3A is a plan view showing the first shape of a liquid crystal shutter forming a field stop in the surgical microscope according to the first embodiment;

FIG. 3B is a plan view showing the second shape of the liquid crystal shutter;

FIG. 4A is a plan view showing the display state of a microscopic observation image on the surgical microscope according to the first embodiment;

FIG. 4B is a plan view showing a state in which a microscopic image and an LCD monitor image are simultaneously displayed on the surgical microscope according to the first embodiment;

FIG. 11A is a plan view showing the first shape obtained by forming a circular light-transmitting portion and light-shielding portion in an LCD shutter forming a field stop in the surgical microscope according to the second embodiment;

FIG. 11B is a plan view showing a state in which a light-attenuating portion is formed in part of the light-transmitting portion of the LCD shutter;

FIG. 12 is a view showing the overall arrangement of a surgical microscope and an endoscope according to the third embodiment of the present invention;

FIG. 13 is a front view of the eyepiece lens barrel of the surgical microscope according to the third embodiment;

FIG. 14 is a plan view of the eyepiece lens portion of the surgical microscope in FIG. 13;

FIG. 15 is a side view of the eyepiece lens portion of the surgical microscope in FIG. 13;

FIG. 28 is a side view of the eyepiece lens barrel in FIG. 27;

FIG. 29 is a side view of the eyepiece lens barrel of a surgical microscope according to the seventh embodiment of the present invention;

FIGS. 30A and 30B are views each showing the observation state of the surgical microscope in FIG. 29;

FIGS. 31A and 31B are views showing states in which the monitor display windows in FIGS. 30A and 30B are corrected;

DETAILED DESCRIPTION OF THE INVENTION

Figure 1:
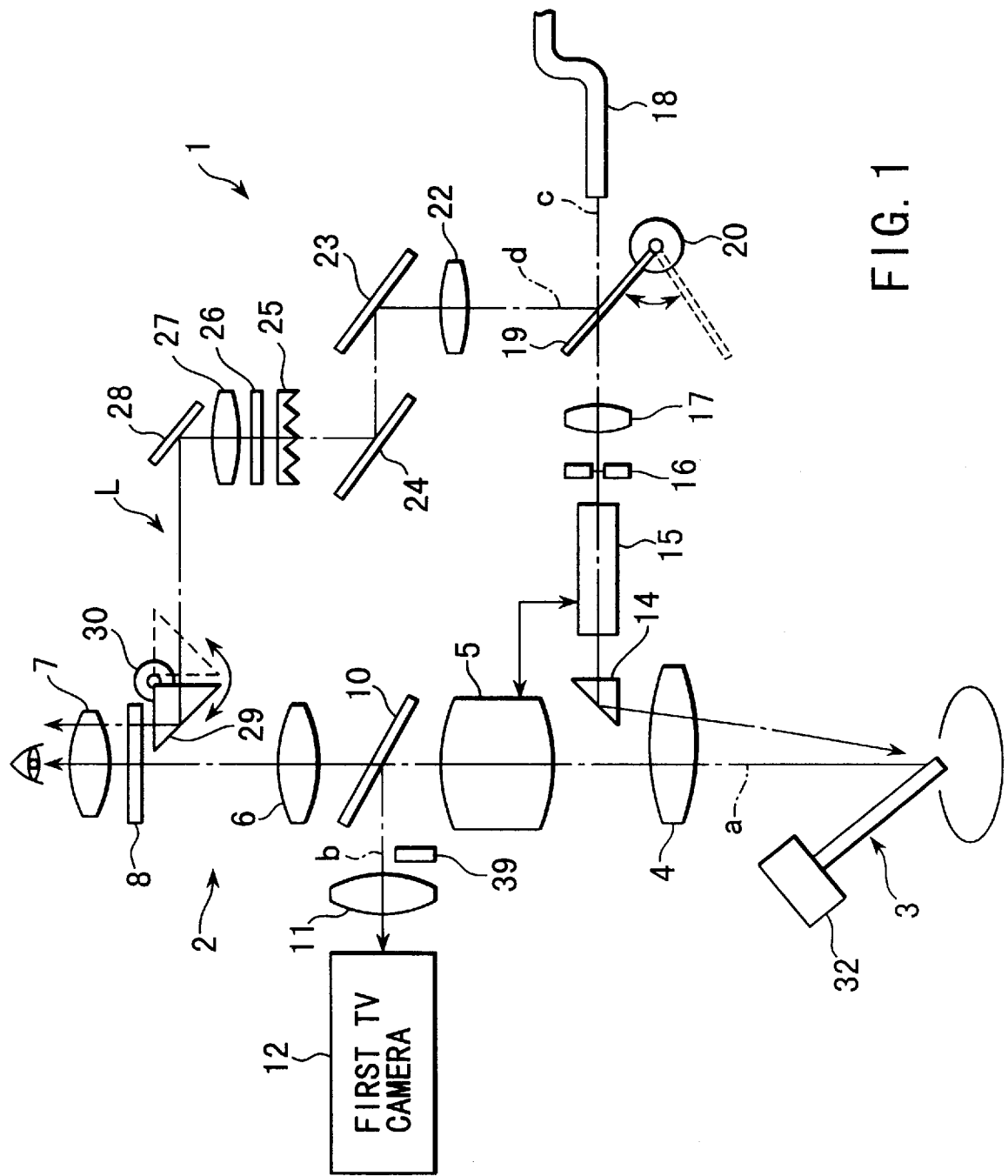
FIG. 1 is a view showing the schematic arrangement of a surgical microscope for a microsurgery using an endoscope as well according to the first embodiment of the present invention.

The first embodiment of the present invention will be described below with reference to FIGS. 1 to 4A and 4B. FIG. 1 shows the schematic arrangement of a surgical microscope system 1 for microsurgery using an endoscope in this embodiment. The surgical microscope system 1 includes a surgical microscope 2 and a hard endoscope (endoscope) 3 used in conjunction with the surgical microscope 2.

The microscope optical system of the surgical microscope 2 comprises an objective lens 4, a zoom optical system 5, an imaging lens 6, and an eyepiece lens 7. The microscope optical system (observation optical system) is constituted by two optical systems arranged on the right and left sides to allow stereoscopic observation. Each of the right and left optical systems (FIG. 1 shows only one optical system) includes the zoom optical system 5, the imaging lens 6, and the eyepiece lens 7. Note that since the right and left optical systems have substantially the same arrangement, only one optical system will be described below.

Figure 2:
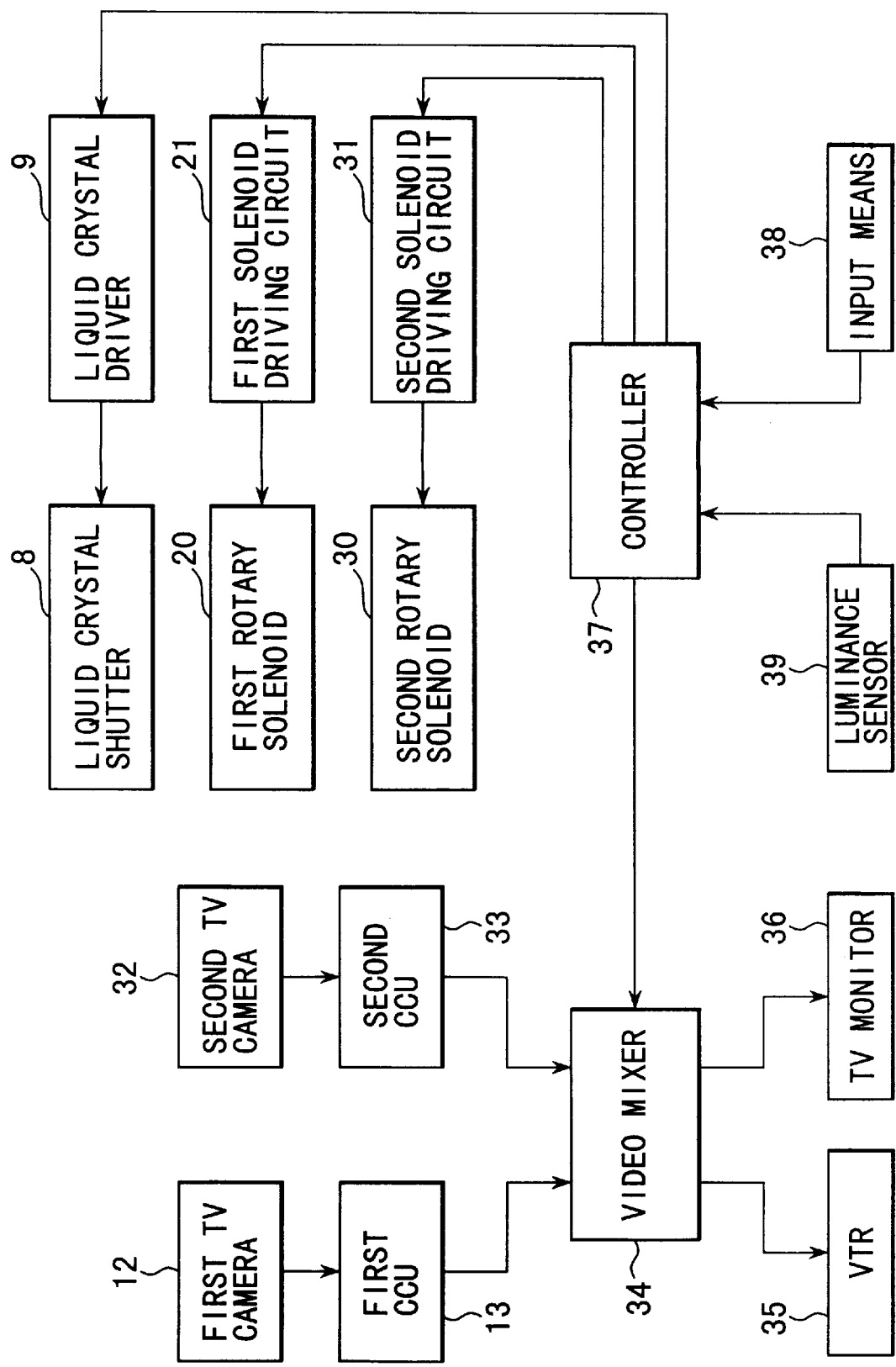
FIG. 2 is a shield diagram showing the control system of a surgical microscope system according to the first embodiment.

Each of the right and left optical systems has a liquid crystal shutter 8 placed at the imaging point of the imaging lens 6 to adjust the field area of the visual field of the microscope. This liquid crystal shutter 8 is connected to a liquid crystal driver 9, as shown in FIG. 2.

A half mirror 10 for deflecting an observation image beam (first optical image beam) in the direction of an optical axis b extending in a direction perpendicular to an optical axis a of the microscope optical system is placed between the zoom optical system 5 and the imaging lens 6. A second imaging lens 11 is placed along the optical axis b from the half mirror 10. A first TV camera 12 is placed at the imaging point of the second imaging lens 11. The first TV camera 12 is connected to a first CCU (Camera Control Unit) 13 (see FIG. 2). Note that the half mirror 10, the second imaging lens 11, and the first TV camera 12 constitute a photographing optical system.

A prism 14 for illumination light is placed behind the objective lens 4 at a position offset from the optical axis a of the microscope optical system. A zoom illumination optical system 15, an illumination field stop 16, a condenser lens 17, and a light guide 18 are sequentially arranged behind the prism 14, thus forming an illumination optical system.

The illumination field stop 16 is placed at a position conjugate to the illumination field of the illumination field stop 16. An interlocking mechanism (not shown) is arranged between the zoom optical system 5 and the zoom illumination optical system 15. Note that the illumination light incident end portion of the light guide 18 is connected to a light source unit (not shown).

A half mirror 19 is interposed between the condenser lens 17 and light guide 18 of the illumination optical system. The half mirror 19 is mounted on the rotating shaft of a first rotary solenoid 20. The first rotary solenoid 20 is connected to a first solenoid driving circuit 21.

The half mirror 19 is supported to be inserted/removed into/from the optical path of the illumination optical system in accordance with the rotation of the first rotary solenoid 20. More specifically, while the first rotary solenoid 20 is OFF, the half mirror 19 is held at a standby position shifted from the illumination optical system, as indicated by the dotted line in FIG. 1. When the first rotary solenoid 20 is ON, the half mirror 19 is pivoted to a set position where the half mirror 19 is inserted into the optical path of the illumination optical system, as indicated by the solid line in FIG. 1. At this time, the half mirror 19 is disposed to deflect part of a light beam from the light guide 18 in a direction (optical path d) perpendicular to an optical axis c of the illumination optical system.

A second condenser lens 22, a pair of mirrors 23 and 24, and an optical diffusing plate 25 are sequentially arranged on the optical path d. The light guided onto the optical path d forms backlight for an LCD monitor 26 (to be described later).

The LCD monitor 26 is disposed near the optical diffusing plate 25 in its diffusion direction. The LCD monitor 26 is connected to an image selector (not shown) through an LCD driver (not shown). The LCD monitor 26 can display various images (second optical images), e.g., endoscopic images, diagnostic images before and during surgical operations (MRI images, CT images, X-ray images, fluorescent observation images, and the like), navigation images, a computer window, patient's vital data (bloodstream, respiration rate, pulse rate, body temperature, and the like), and a timepiece window. An imaging lens 27, a mirror 28, and a prism 29 are sequentially arranged behind the LCD monitor 26, thus forming an image projection optical system L for projecting an image onto part of the visual field of the microscope.

The prism 29 is mounted on the rotating shaft of a second rotary solenoid 30 and is inserted/removed into/from the optical path (optical axis a) of the microscope optical system in accordance with the rotation of the second rotary solenoid 30. More specifically, while the second rotary solenoid 30 is OFF, the prism 29 is held at a standby position shifted from the microscope optical system, as indicated by the dotted line in FIG. 1. When the second rotary solenoid 30 is ON, the prism 29 is pivoted to a set position where the prism 29 is partly inserted into the optical path (optical axis a) of the microscope optical system, as indicated by the solid line in FIG. 1. At this time, the prism 29 is disposed such that an image from the LCD monitor 26 is formed on a plane substantially flush with the imaging position of the microscope optical system.

Note that the surfaces of the prism 29 except for the incident and exit surfaces are entirely painted black. The second rotary solenoid 30 is connected to a second solenoid driving circuit 31.

To perform both observation with the surgical microscope 2 and observation with the endoscope, the hard endoscope 3 is inserted into a region during operation of the surgical microscope 2. While the hard endoscope 3 is used, a second TV camera 32 is mounted on the proximal end portion of the hard endoscope 3. As shown in FIG. 2, the TV camera 32 is connected to a second CCU 33. The second CCU 33 of the TV camera 32 and the first TV camera 12 as a component of the image sensing optical system are connected to a video mixer 34. A VTR 35 and a TV monitor 36 are connected to the video mixer 34.

A microscope frame incorporates a controller 37. An input means 38 including a focus switch, zoom switch, and observation mode switch (not shown), the first solenoid driving circuit 21, the second solenoid driving circuit 31, the liquid crystal driver 9, and the video mixer 34 are connected to the controller 37.

As shown in FIG. 1, a luminance sensor 39 is placed between the half mirror 10 and the second imaging lens 11 of the image sensing optical system of the microscope 2. The luminance sensor 39 is connected to the controller 37 (see FIG. 2). The controller 37 drives the second rotary solenoid 30 to change the shape of the liquid crystal shutter 8 in accordance with the operation of the observation mode switch (not shown) of the input means 38, e.g., the operation of switching the mode of using only the surgical microscope 2 to the mode of using both the surgical microscope 2 and the hard endoscope 3.

The function of the system 1 having the above arrangement will be described next. In using the surgical microscope system 1 of this embodiment, the operator moves the microscope frame (not shown) to position the microscope optical system of the surgical microscope 2 above a region, and observes the region.

When the region is to be observed, the observation light emitted from a light source unit (not shown) emerges from the light guide 18. While the first rotary solenoid 20 is OFF, the half mirror 19 is held at the standby position offset from the illumination optical system, as indicated by the dotted line in FIG. 1. The entire observation light emerging from the light guide 18 is focused by the condenser lens 17 and applied to the region through the illumination field stop 16, the zoom illumination optical system 15, the prism 14, and the objective lens 4. In this state, the observation light conforming to the shape of the illumination field stop 16 is guided, in a proper size corresponding to the zoom optical system 5 as a component of the microscope optical system, to the region by the zoom illumination optical system 15.

The observation light reflected by the region strikes the objective lens 4 and is guided to an eye of the operator through the zoom optical system 5, the imaging lens 6, the liquid crystal shutter 8, and the eyepiece lens 7, thereby allowing observation of the region under magnification. At this time, the liquid crystal shutter 8 is shaped as shown in FIG. 3A in accordance with the output from the liquid crystal driver 9. That is, the liquid crystal shutter 8 has a circular light-transmitting portion 41 that perfectly transmits light and a light-shielding portion 42 formed around the light-transmitting portion 41. Light is completely shielded by the light-shielding portion 42. The inner diameter of the circular light-transmitting portion 41 is set to be slightly smaller than the diameter of an image circle 40 (indicated by the dotted line in FIG. 3A) on the imaging plane formed by the microscope optical system. The liquid crystal shutter 8 serves as the field stop of the microscope optical system by completely shielding light with the light-shielding portion 42 outside the light-transmitting portion 41. With this arrangement, the operator can obtain a microscopic observation image that is made sharp up to its periphery.

While the region is observed under magnification, the half mirror 10 deflects part of the observation light beam passing through the microscope optical system in the direction of the optical axis b extending in a direction perpendicular to the optical axis a of the microscope optical system. The light beam deflected by the half mirror 10 is formed into an image on the image sensing element (not shown) of the first TV camera 12 through the second imaging lens 11. The microscopic observation image formed on the image sensing element is converted into an electrical signal and sent to the first CCU 13.

The first CCU 13 converts the received electrical signal into a video signal and outputs it to the video mixer 34. In this state, since the hard endoscope 3 is not used, the video mixer 34 outputs only the microscopic observation image to the TV monitor 36 and the VTR 35. A nurse and the like can therefore observe the state of the region by visually checking a microscopic observation image P. The state of the region (microscopic observation image P) can be recorded by the VTR 35, as needed.

When the endoscope is to be concurrently used to observe a blind spot of the microscope 2, the operator holds the hard endoscope 3 mounted on the microscope holder or the like (not shown) with his/her hand and inserts it into the region. In this case, the operator inserts the hard endoscope 3 into the region with greatest care so as not to damage the neighboring tissue, and introduces it to a desired observation position. During this operation, the second TV camera 32 mounted on the hard endoscope 3 senses an image (endoscopic image) of the hard endoscope 3 and outputs the video signal to the video mixer 34 through the second CCU 33. When the observation mode switch (not shown) mounted on the input means 38 is operated, the controller 37 receives a signal from the switch and outputs driving (control) signals to the first solenoid driving circuit 21, the second solenoid driving circuit 31, the liquid crystal driver 9, and the video mixer 34.

Upon reception of the driving signals, the first solenoid driving circuit 21 and the second solenoid driving circuit 31 supply driving power to the first and second rotary solenoids 20 and 30. As a result, the first and second rotary solenoids 20 and 30 are turned on.

When the first rotary solenoid 20 is turned on, the half mirror 19 is inserted into the optical path of the illumination optical system, and part of the illumination light is deflected in the direction of the condenser lens 22. The deflected illumination light is focused by the condenser lens 22 and guided to the optical diffusing plate 25 through the mirrors 23 and 24. The illumination light beam incident on the optical diffusing plate 25 is reflected diffusely. The light reflected diffusely by the optical diffusing plate 25 serves as backlight for the LCD monitor 26.

An arbitrary image selected by an image selector (not shown) can be projected on the LCD monitor 26. In this embodiment, an endoscopic image is projected on the LCD monitor 26 by a selector function (not shown).

When the second rotary solenoid 30 is turned on, together with the first rotary solenoid 20, the prism 29 is inserted into part of the light beam from the microscope optical system. As a result, the endoscopic image projected on the LCD monitor 26 is formed on the liquid crystal shutter 8 by the imaging lens 27 through the mirror 28 and the prism 29. In this case, since the prism 29 is painted black, a portion, of the light beam from the microscope optical system, which is vignetted by the prism 29 is absorbed by the prism 29 and does not reach the liquid crystal shutter 8. Note that the light beam from the microscope optical system is also formed into an image on the liquid crystal shutter 8 at a plane substantially flush with the imaging position of the endoscope.

Upon reception of the control signal from the controller 37, the liquid crystal driver 9 changes the transmittance of the liquid crystal shutter 8 as shown in FIG. 3B. In this embodiment, a light-transmitting portion 43 that perfectly transmits a light beam is formed on the upper left of the visual field of the liquid crystal shutter 8. An area where the endoscopic image projected on the LCD monitor 26 is formed is placed in the light-transmitting portion 43.

A light-attenuating portion 44 that attenuates light at a predetermined ratio is formed on a portion, of the circular area slightly smaller than the image circle 40 (indicated by the dotted line in FIG. 3B) formed by the microscope optical system, other than the light-transmitting portion 43 serving as the imaging area for the LCD monitor 26. A light-shielding portion 45 that completely shields light is formed on a portion of the liquid crystal shutter 8 other than the light-transmitting portion 43 and the light-attenuating portion 44.

The attenuation ratio of the light-attenuating portion 44 is determined as follows. The illuminance of an observation light beam is detected by the luminance sensor 39 between the half mirror 10 and second imaging lens 11 as components of the photographing optical system. The detection data from the luminance sensor 39 is input to the controller 37. The controller 37 computes the luminance data from the luminance sensor 39 and outputs a control signal to the liquid crystal driver 9 to set the luminances of the microscopic image and monitor image at the optimal ratio for the operator. With this operation, the operator can simultaneously observe the microscopic image and the LCD monitor image (the observation image obtained with the hard endoscope 3) formed on the liquid crystal shutter 8 at the optimal light amount ratio through the eyepiece lens 7.

When the surgical microscope 2 and the hard endoscope 3 are used concurrently in this manner, the microscopic image sensed by the first TV camera 12 and the endoscopic image sensed by the second TV camera 32 are input to the video mixer 34. Upon reception of the control signal from the controller 37 in this state, the video mixer 34 switches the image modes for output operation for the TV monitor 36 and the VTR 35 as follows. As described above, when the surgical microscope 2 is to be used alone, the video mixer 34 maintains the image mode for entire window display, in which only the microscopic image is output to the display screen of the TV monitor 36 as shown in FIG. 4A. When the surgical microscope 2 and the hard endoscope 3 are to be used together, the video mixer 34 is switched to the image mode for master/subsidiary window display, in which a master window 46 having a large display area and a subsidiary window 47 having a display area smaller than that of the master window 46 are formed on the display screen of the TV monitor 36, as shown in FIG. 4B, in response to the control signal from the controller 37. In this embodiment, the windows are displayed on the TV monitor 36 in the same manner in which the operator observes the region with the naked eye. That is, the microscopic image is displayed in the master window 46, and at the same time, the subsidiary window 47 is located at the upper left position in the visual field of the master window 46. The endoscopic image is displayed in the subsidiary window 47. The video signal of the master and subsidiary windows on the TV monitor 36 is also sent to the VTR 35 to be recorded.

As described above, in this embodiment, the controller 37 for changing the shape of the liquid crystal shutter 8 upon interlocking with the operation of the second rotary solenoid 30 is used to change the field stop of the image projection optical system L by means of the liquid crystal shutter 8 as follows. In the normal microscopic observation mode, the shape of the liquid crystal shutter 8 is set as shown in FIG. 3A to obtain a circular visual field formed by the circular field stop including the circular light-transmitting portion 41 and the peripheral light-shielding portion 42. When the surgical microscope 2 and the hard endoscope 3 are to be used together, the shape of the field stop of the liquid crystal shutter 8 is changed as shown in FIG. 3B to allow simultaneous display of the image from the LCD monitor 26 and the microscopic observation image. With this arrangement, since visual fields that are not restricted by the general image circle 40 can be obtained, the degree of freedom increases in terms of the imaging position of an image from the LCD monitor 26. In addition, vignetting of a microscopic observation image obtained when endoscopic observation is also performed can be minimized, and a proper visual field can be obtained by shifting the imaging position of the LCD monitor 26 outside the visual field of -the microscope as far as possible within the performance of the eyepiece lens 7. In the microscopic observation mode, an optical image comparable in quality to a general microscopic image can be obtained.

In this embodiment, since illumination light from the microscope light source is used as backlight for the LCD monitor 26, there is no need to prepare a backlight source incorporating an inverter and the like. Heat generation in the mirror barrel portion can therefore be suppressed.

When an image on the LCD monitor 26, e.g., an endoscopic image, is to be observed, light is only required to orient the endoscope, and hence an illumination amount as large as that in general microscopic observation is not required. If, therefore, a surplus amount of light is used for backlight as in this embodiment, the illumination efficiency improves.

In this embodiment, since the excessive difference between the brightness of a microscopic observation image and that of an endoscopic image from the LCD monitor 26 makes it difficult to perform observation, the transmittance of the liquid crystal shutter 8 is automatically changed in accordance with the brightness of each observation image. Therefore, the operator can always observe both images with the optimal brightness, and can efficiently perform a surgical operation.

Furthermore, in this embodiment, in simultaneously observing an endoscopic image, a person can obtain the same visual field as that of the operator with respect to images on the TV monitor 36 and the VTR 35. This serves an educationally useful function for students and greatly improves the efficiency in provision of assistance from assistants, nurses, and the like, producing great effects, e.g., shortening the operation time and reducing the loads on the operator and the patient.

This embodiment has exemplified only the case wherein microscopic image light is attenuated on the premise that a microscopic image is generally brighter than an LCD monitor image. When, however, a relatively dark image such as a red-reflex image is to be observed as in a case wherein the present invention is applied to ophthalmology, this relationship may be reversed. Such a case can be handled by changing the relationship between the light-attenuating portion 44 and the light-transmitting portion 43.

In this embodiment, the liquid crystal shutter 8 serving also as a field stop is placed at both the imaging positions of the surgical microscope 2 and the hard endoscope 3 to control the brightness of each of the observation images obtained by the surgical microscope 2 and the hard endoscope 3. However, a member (brightness control member) for controlling brightness may be placed independently of a field stop. For example, a liquid crystal shutter or detachable ND filter may be placed at the afocal light beam portion of a microscopic optical image. With this arrangement, since no dot expansion of the brightness control member due to the eyepiece lens 7 occurs, a liquid crystal shutter with relatively coarse dots can be used without any problems. This allows a reduction in cost. In addition, when an ND filter is used, since no liquid crystal driver is required, a further reduction in cost can be attained with high reliability.

Figure 5:
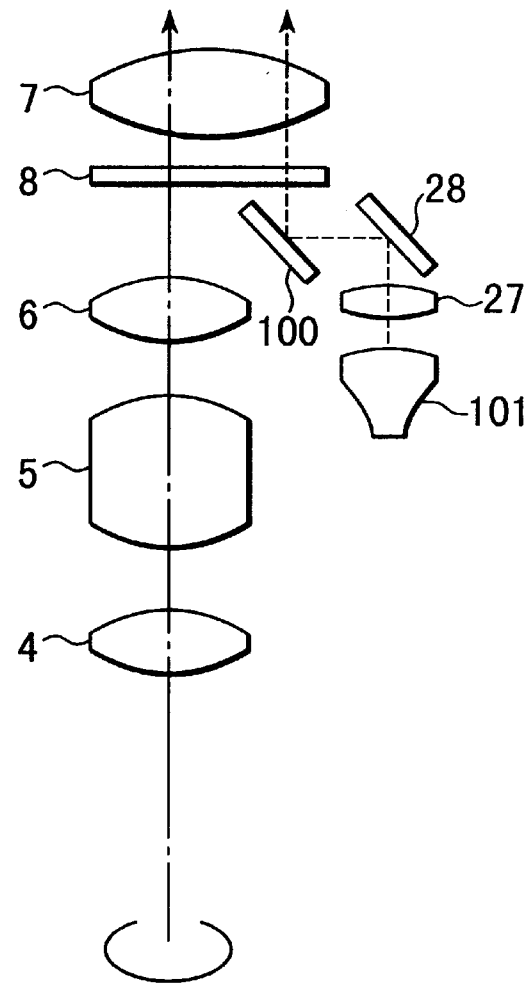
FIG. 5 is a view showing the arrangement of the main part of a modification of the first embodiment.
Figure 6A:
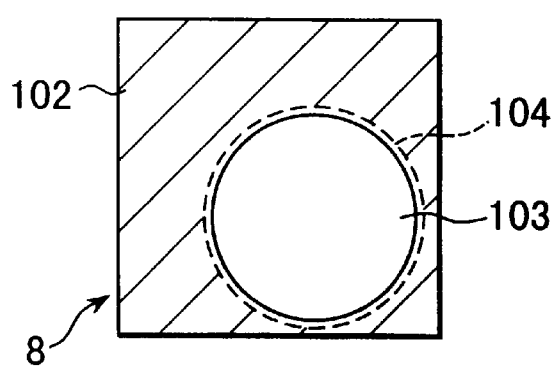
FIG. 6A is a plan view showing the first shape of a liquid crystal shutter forming a field stop in the arrangement shown in FIG. 5.
Figure 6B:
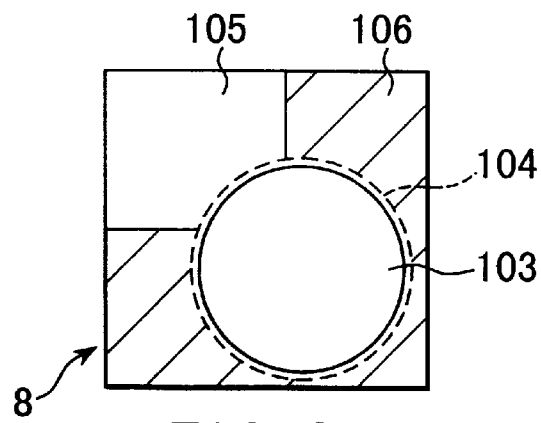
FIG. 6B is a plan view showing the second shape of the liquid crystal shutter.

In this embodiment, a window on the liquid crystal display is displayed while being inserted/removed into/from a microscopic observation image. However, the present invention is not limited to this. That is, as shown in FIG. 5, a fixed mirror 100 may be used in place of the movable prism 29, and the LCD monitor 26 may be replaced with another display means, e.g., a CRT display 101. In this arrangement, when no image observation is to be performed, the liquid crystal shutter 8 is controlled as shown in FIG. 6A to allow the operator to observe only a microscopic optical image. More specifically, the liquid crystal shutter 8 is controlled to have a light-shielding portion 102 indicated by the hatching and a light-transmitting portion 103 slightly smaller than a microscopic image circle 104. When microscopic observation and image observation are to be performed at once, the liquid crystal shutter 8 is controlled as shown in FIG. 6B to allow the operator to observe an image through a second light-transmitting portion 105 as well as a microscopic optical image. More specifically, the light beam emerging from the CRT display 101 is guided to the eyepiece lens 7 through the imaging lens 27, the mirror 28, the mirror 100, and the second light-transmitting portion 105 of the liquid crystal shutter 8 so as to be observed at the upper left of the microscopic observation image. Reference numeral 106 denotes a light-shielding portion to be formed when microscopic observation and image observation are preformed concurrently. As described above, according to the arrangement shown in FIG. 5, since the prism inserting/removing mechanism can be omitted, reductions in size, weight, and cost can be attained.

FIGS. 7 to 11A and 11B show the second embodiment of the present invention. This embodiment is a modification of the first embodiment. The same reference numerals in the second embodiment denote the same parts as in the first embodiment, and a description thereof will be omitted.

In this embodiment, one objective lens 4 is placed below the lower surface of a microscope body 51 of a surgical microscope 2, and a pair of right and left eyepiece lenses 7 (for the right and left eyes) are arranged above the upper surface of the microscope body 51. Right and left observation optical systems 52R and 52L constituting a microscope optical system are arranged between the objective lens 4 and the right and left eyepiece lenses 7. Note that since the observation optical systems 52L and 52R have the same arrangement, only the observation optical system 52L for the left eye will be described below unless required.

In the observation optical system 52L for the left eye, a zoom optical system 5, a prism 53, and an imaging lens 6 are sequentially arranged. The prism 53 is disposed to pivot about an axis al on the extended line of the optical axis of the zoom optical system 5. The prism 53 of the observation optical system 52R for the right eye is placed to pivot about an axis $a_2$ on the extended line of the optical axis of the zoom optical system 5 in the same observation optical system.

Figure 9:
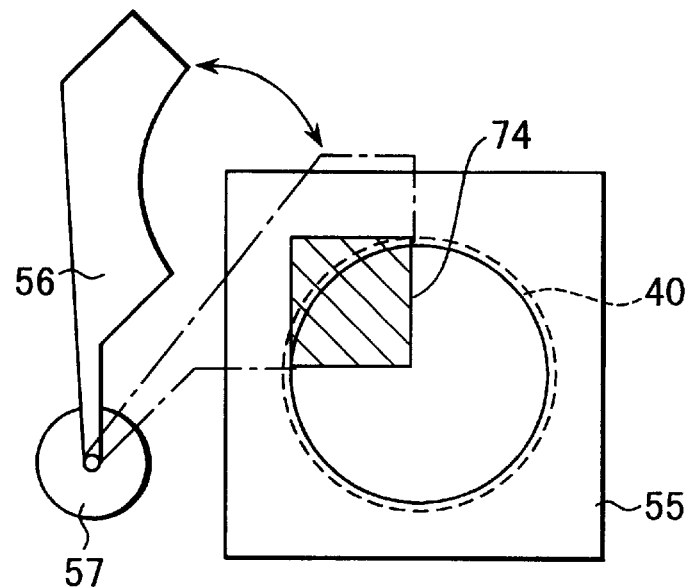
FIG. 9 is a view for explaining the arrangement and operation of a field stop in the surgical microscope according to the second embodiment.

A first luminance sensor 54 (to be described later) is arranged between the prism 53 and the imaging lens 6. First and second field stops 55 and 56 are arranged between the imaging lens 6 and the eyepiece lens 7. The first field stop 55 is fixed to the imaging plane of the imaging lens 6 and is shaped to ensure a visual field for a light beam from the microscope optical system and a light beam from an LCD monitor 26 (to be described later), as shown in FIG. 9. One end of the second field stop 56 is mounted on the shaft of a first rotary solenoid 57 to be pivoted by the rotary solenoid 57. More specifically, the second field stop 56 is held at the set position indicated by the chain line in FIG. 9 while the rotary solenoid 57 is OFF, and is pivoted to the standby position indicated by the solid line in FIG. 9 when the rotary solenoid 56 is ON. Note that the first and second field stops 56 are substantially flush with each other.

In this embodiment, as in the first embodiment, a monitor observation optical system (image projection optical system) is constituted by the LCD monitor 26, an imaging lens 27, a mirror 28, and a prism 29. The prism 29 is mounted on the rotating shaft of a second rotary solenoid 30 and is inserted/removed into/from the optical path of the microscope optical system upon rotation of the solenoid 30. In this embodiment, a backlight 58 for the LCD monitor 26 is disposed within a plane perpendicular to the axes $a_1$ and $a_2$ in the microscope optical system. Two prisms 59 (for the right and left eyes) are arranged above the backlight 58. One end of each of the prisms 59 is supported to be pivotal about the axes $a_1$ and $a_2$. The other end of each of the prisms 59 faces the lower surface of the LCD monitor 26 at a distance therefrom. A second luminance sensor 60 is mounted between the LCD monitor 26 and the imaging lens 27.

The prism 53 and the prism 59 are interlocked with each other through an interlocking mechanism (not shown). The LCD monitor 26, the second luminance sensor 60, the imaging lens 27, the mirror 28, the prism 29, and the second rotary solenoid 30 constituting the monitor observation optical system are arranged on the pivot end side of the prism 59. This system is driven upon interlocking with the prism 59.

Figure 8:
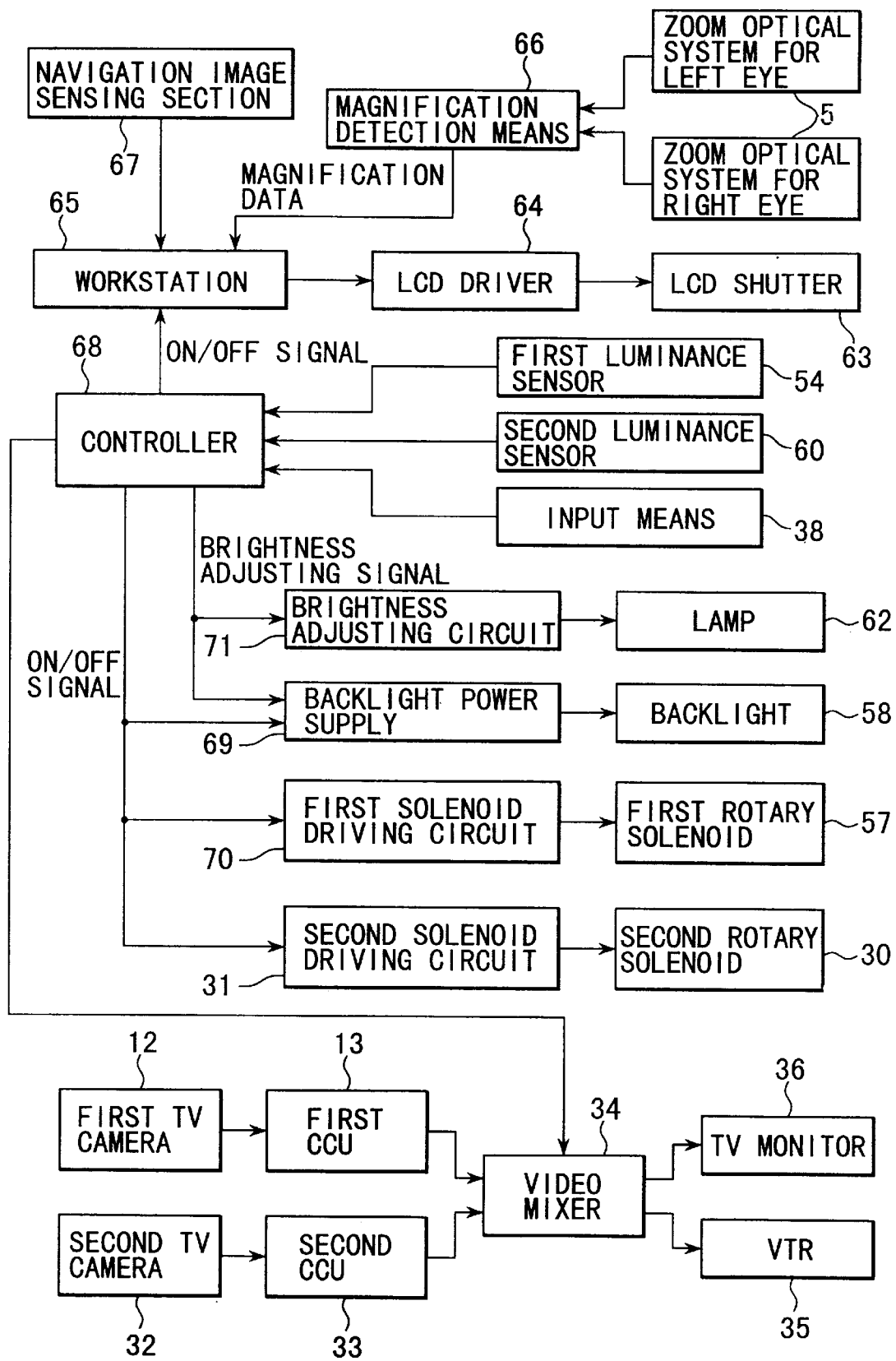
FIG. 8 is a shield diagram showing the control system of the surgical microscope system according to the second embodiment.

A beam splitter 61 is inserted between the right and left zoom optical systems 5 and prism 53 of the microscope optical system. The beam splitter 61 is positioned to deflect part of a light beam from the microscope optical system in a direction (the direction of an optical axis b) perpendicular to the light beam. A second imaging lens 11 is placed along the optical axis b from the beam splitter 61. A first TV camera 12 is placed at the imaging plane of the second imaging lens 11. As shown in FIG. 8, the first TV camera 12 is connected to a first CCU 13. As in the first embodiment, the first CCU 13 is connected to a video mixer 34.

The illumination optical system of this embodiment has a lamp 62 incorporated in the microscope body 51 of the surgical microscope 2. As in the first embodiment, a prism 14 for illumination light is placed at a position offset from the optical axes $a_1$ and $a_2$ of the microscope optical system. A zoom illumination optical system 15 is placed behind the prism 14.

An LCD shutter 63 is placed at a position conjugate to the illumination field in which an illumination field stop 16 is placed in the first embodiment. The LCD shutter 63 is switched between the first state shown in FIG. 11A and the second state shown in FIG. 11B. More specifically, in the first state shown in FIG. 11A, a circular light-transmitting portion 63a is formed, together with a light-shielding portion 63b formed around the light-transmitting portion 63a. When the LCD shutter 63 is switched to the state shown in FIG. 11B, a light-attenuating portion 63c having an arbitrary size is formed at an arbitrary position within the light-transmitting portion 63a. A condenser lens 17 is disposed between the LCD shutter 63 and the lamp 62. Note that the zoom illumination optical system 15 is interlocked with the zoom optical system 5 of the microscope optical system through an interlocking mechanism (not shown) as in the first embodiment.

As shown in FIG. 8, the LCD shutter 63 is connected to an LCD driver 64. The LCD driver 64 is connected to a workstation 65 for navigation. A magnification detection means 66 is provided for the right and left zoom optical systems 5 of the microscope optical system. The magnification detection means 66 is connected to the workstation 65. A navigation image sensing section 67 and a controller 68 are connected to the workstation 65. The first luminance sensor 54, the second luminance sensor 60, an input means 38, and a video mixer 34 are connected to the controller 68.

The backlight 58 is connected to a backlight power supply 69 incorporating a brightness adjusting circuit. A second rotary solenoid 30 is connected to a second solenoid driving circuit 31. The first rotary solenoid 57 is connected to a first solenoid driving circuit 70. The backlight power supply 69, the second solenoid driving circuit 31, and the first solenoid driving circuit 70 are connected to the controller 68. The lamp 62 is connected to a brightness adjusting circuit 71. The brightness adjusting circuit 71 is connected to the controller 68.

A hard endoscope 3, a second TV camera 32, and a second CCU 33 respectively have the same arrangements as those in the first embodiment. The second CCU 33 is connected to the video mixer 34. A VTR 35 and a ITV monitor 36 are connected to the video mixer 34. In this embodiment, a marker 72 for hard endoscope navigation is mounted on the hard endoscope 3. A marker 73 for microscope navigation is mounted on the microscope body 51 of the microscope 2.

The function of the surgical microscope system 1 of this embodiment will be described next.

In using the surgical microscope system 1 of this embodiment, the operator moves the microscope frame (not shown) to position the microscope optical system of the surgical microscope 2 above a region, and observes the region. In observing the region, the illumination light emitted from the lamp 62 is focused by the condenser lens 17 and applied to the region through the LCD shutter 63, the zoom illumination optical system 15, the prism 14, and the objective lens 4. At this time, the LCD shutter 63 is held in the first state in FIG. 11A by the LCD driver 64. In the first state, the illumination light transmitted through the light-transmitting portion 63a of the LCD shutter 63 is applied to the region, and the illumination light incident on the light-shielding portion 63b is shielded. Since the LCD shutter 63 is located at a position conjugate to the illumination field plane, the shape (circle in this embodiment) of the light-transmitting portion 63a is projected on the illumination field plane. The LCD shutter 63 therefore serves as an illumination field stop. Other functions of the LCD shutter 63 are the same as those in the first embodiment.

The observation light reflected by the region is incident on the objective lens 4 and guided to an eye of the operator through the zoom optical system 5, the beam splitter 61, the prism 53, the imaging lens 6, the first field stop 55, the second field stop 56, and the eyepiece lens 7. This allows observation of the region under magnification. At this time, since the first rotary solenoid 57 is held in the OFF state, the second field stop 56 is located at the position indicated by the chain line in FIG. 9. The field stop formed by the first and second field stops 56 is slightly smaller than an image circle 40 formed by the microscope optical system. Hence, the operator can obtain a microscopic observation image that is made sharp up to its periphery.

Part of the light beam deflected by the beam splitter 61 is incident on the first TV camera 12 through the second imaging lens 11 and converted into an electrical signal by an image sensing element (not shown). This electrical signal is sent to the first CCU 13. The first CCU 13 converts the received electrical signal into a standard video signal and outputs it to the video mixer 34. In this state, since the endoscope is not used, the video mixer 34 outputs only the microscopic observation image to the TV monitor 36 as in the first embodiment. A nurse and the like can therefore observe the state of the region by visually checking the display screen of the TV monitor 36.

At this time, the navigation image sensing section 67 senses the marker 73 attached to the microscope body 51 of the surgical microscope 2 by using three image sensing elements (not shown), and sends the resultant data to the workstation 65. The workstation 65 calculates the position of the microscope body 51 of the surgical microscope 2 and the observation position of the surgical microscope 2 on the basis of the received data. The calculation results are displayed on a monitor (not shown) or the like, and the operator can specify the current treatment region on an image such as a pre-diagnostic image.

When the endoscope is to be used together with the microscope 2 to observe a blind spot of the microscope 2, the operator holds the hard endoscope 3 mounted on the endoscope holder or the like (not shown) with his/her hand and inserts it into the region. During insertion of the hard endoscope 3, the second TV camera 32 mounted on the hard endoscope 3 senses the observation image obtained by the hard endoscope 3, and outputs the video signal to the video mixer 34 through the second CCU 33. In this case, the operator inserts the hard endoscope 3 into the region with great care while observing with the microscope so as not to damage the neighboring tissue.

During insertion of the hard endoscope 3, the navigation image sensing section 67 senses the marker 72 attached to the hard endoscope 3 by using the three image sensing elements (not shown), and sends the resultant data to the workstation 65. At the same time, a marker 73 for the microscope is also sensed by the navigation image sensing section 67, and the resultant data is sent to the workstation 65. The workstation 65 calculates the position of the microscope body 51 of the surgical microscope 2, the observation position of the surgical microscope 2, the position of the distal end of the hard endoscope 3, and the observation position of the hard endoscope 3 on the basis of the received data on the marker 73 for the microscope and the data on the marker 72 on the hard endoscope 3.

Upon detecting a state in which the observation position of the hard endoscope 3 overlaps the observation position of the microscope 2, the workstation 65 outputs a control signal to the LCD driver 64. Upon reception of the control signal, the LCD driver 64 controls the LCD shutter 63 to switch its state from the first state in FIG. 11A to the second state in FIG. 11B. That is, the light-attenuating portion 63c is formed on part of the light-transmitting portion 63a of the LCD shutter 63. The size and position of the light-attenuating portion 63c vary depending on the size and position of the observation portion of the hard endoscope 3 with respect to the observation field of the surgical microscope 2, and are controlled by a control signal from the workstation 65.

Figure 10A:
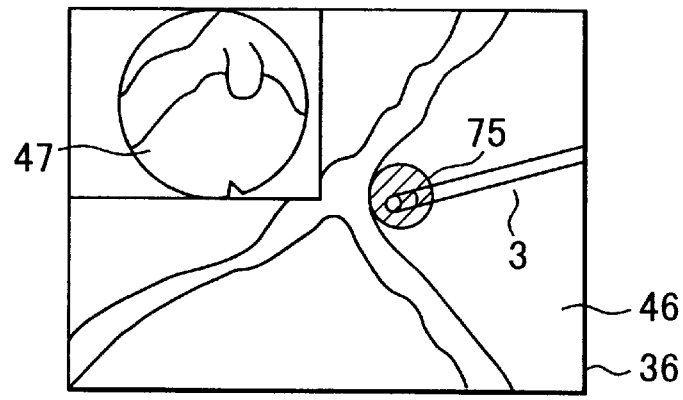
FIG. 10A is a plan view showing a display state in which a microscopic image and an endoscopic image are simultaneously displayed on the surgical microscope according to the second embodiment while microscope illumination light is attenuated at the distal end position of a hard endoscope.
Figure 10B:
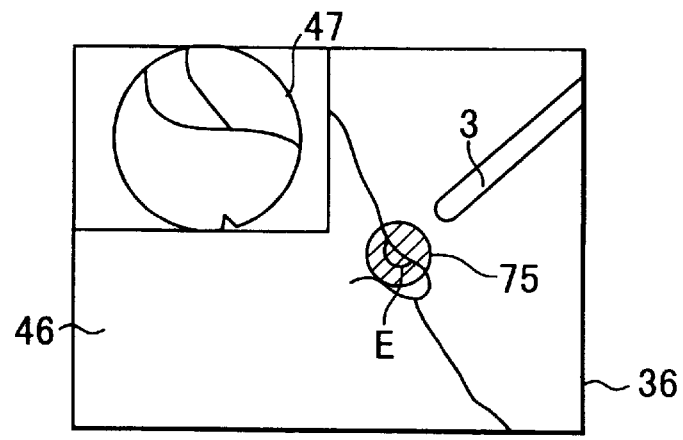
FIG. 10B is a plan view showing a state in which a microscopic image and an endoscopic image are respectively displayed in master and subsidiary windows.

The workstation 65 calculates information indicating the relationship between the observation position of the hard endoscope 3 and the position of the LCD shutter 63 for forming an illumination field stop, i.e., information indicating whether the observation position of the hard endoscope 3 corresponds to the position of the LCD shutter 63, on the basis of the detected data on the observation positions of the surgical microscope 2 and the hard endoscope 3. The workstation 65 then continuously designates the data on the observation position of the hard endoscope 3 on the LCD shutter 63 to the LCD driver 64. In this case, the workstation 65 receives data on the size of the light-attenuating portion 63c from the magnification detection means 66 mounted on the zoom optical system 5, calculates the ratio of the endoscopic observation portion to the microscopic observation range, and continuously instructs the LCD driver 64. With this operation, as shown in FIG. 10B, illumination light on the microscope is always attenuated at an observation portion E of the hard endoscope 3.

When the operator operates the observation mode switch (not shown) mounted on the input means 38 after guiding the hard endoscope 3 to a desired observation position while watching a microscopic image, the controller 68 receives the resultant signal and outputs driving (control) signals to the video mixer 34, the backlight power supply 69, the second solenoid driving circuit 31, and the first solenoid driving circuit 70. Upon reception of the signal from the controller 68, the video mixer 34 switches the display screen of the TV monitor 36 to the image mode for master/subsidiary window display as in the first embodiment. As a result, as shown in FIGS. 10A and 10B, a microscopic image is displayed in a master window 46 having a large display area, and an endoscopic image is displayed on a subsidiary window 47 placed at an upper left position with respect to the visual field of the master window 46.

Upon reception of the driving signal from the controller 68, the backlight power supply 69 supplies power to the backlight 58. As a result, the backlight 58 is turned on. When the backlight 58 is turned on, the light beam emitted from the backlight 58 is applied to the LCD monitor 26 through the prism 59. At the same time, upon reception of the driving signals from the controller 68, the second solenoid driving circuit 31 and the first solenoid driving circuit 70 respectively supply driving power to the second rotary solenoid 30 and the first rotary solenoid 57. As a result, the second rotary solenoid 30 and the first rotary solenoid 57 are turned on.

Figure 7:
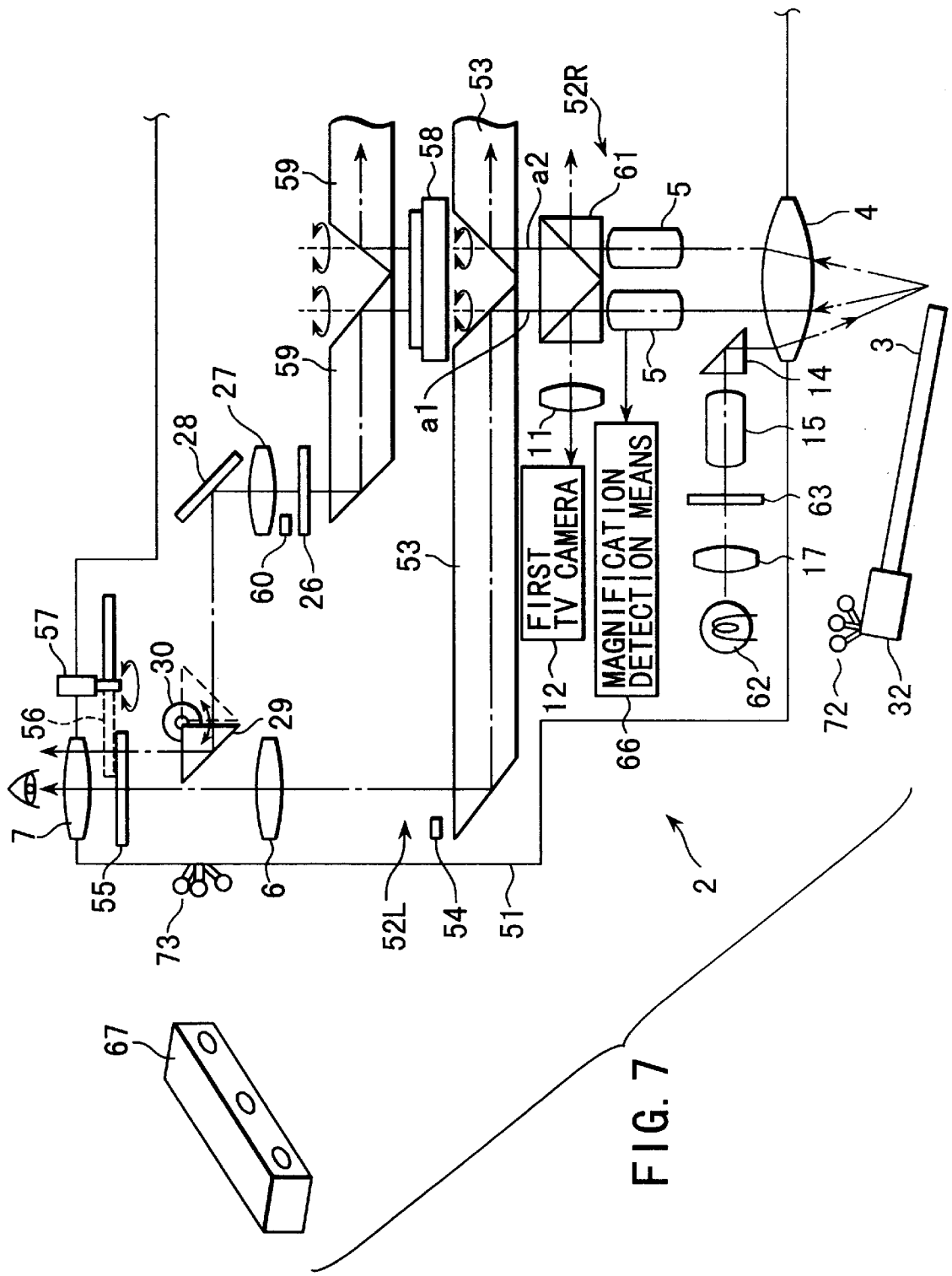
FIG. 7 is a view showing the schematic arrangement of a surgical microscope system according to the second embodiment of the present invention.

When the second rotary solenoid 30 is turned on, the prism 29 is pivoted from the position indicated by the dotted line to the position indicated by the solid line in FIG. 7 as in the first embodiment. With this operation, image light from the LCD monitor 26 irradiated with the light from the backlight 58 is formed into an image at the LCD imaging position 74 flush with the first field stop 55 through the imaging lens 27, the mirror 28, and the prism 29. As in the first embodiment, although various images can be displayed on the LCD monitor 26, the endoscopic image observed with the hard endoscope 3 is selected by an image selector (not shown) and displayed in this embodiment. In addition, as in the first embodiment, since the prism 29 is painted black, a portion, of the light beam from the microscope optical system, which is vignetted by the prism 29 does not reach the imaging position at which the field stop is formed.

When the first rotary solenoid 57 is turned on, the second field stop 56 mounted on the shaft of the solenoid 57 moves to the position indicated by the solid line in FIG. 9. That is, the shape of the field stop changes such that the light beam is transmitted through not only the inside of the image circle 40 of the microscopic image but also an LCD imaging position 74. At this time, the controller 68 detects the brightness of the microscopic optical image from the detection signal from the first luminance sensor 54, and the brightness of the image from the LCD monitor 26 from the detection signal from the second luminance sensor 60, and outputs brightness adjusting signals to the brightness adjusting circuit 71 and the backlight power supply 69 to make the respective luminances almost equal to each other. The difference between the optical image from the surgical microscope 2 and the image from the LCD monitor 26 may be properly adjusted by a setting section (not shown) incorporated in the controller 68 because the proper brightness ratio varies depending on a case, the type of image to be projected, the preference of the operator, and the like.

In addition, in this embodiment, when an eye distance adjusting section (not shown) is adjusted to adjust the distance between the right and left eyepiece lenses 7 of the surgical microscope 2, the prism 53 pivots about the axes $a_1$ and $a_2$ on its one end side. In this case, since the luminance sensor 54, the imaging lens 6, the first field stop 55, the second field stop 56, the first rotary solenoid 57, and the eyepiece lens 7 are integrally mounted on the other side (pivot end side) of the prism 53, these components also pivot as the prism 53 pivots, thus allowing proper observation. Furthermore, since the prism 59 pivots about the axes $a_1$ and $a_2$ on its one end side upon interlocking with the prism 53, the LCD monitor 26, the second luminance sensor 60, the imaging lens 27, the mirror 28, the prism 29, and the second rotary solenoid 30, which are mounted on the other end side of the prism 59, move in accordance with the movement of the prism 59. This allows the operator to observe the LCD monitor 26. With these functions, therefore, the operator can simultaneously observe the microscopic optical image through the eyepiece lenses 7 and the endoscopic image projected on the LCD monitor 26 with a proper eye distance and an optimal optical amount ratio.

As described above, in this embodiment, the first and second field stops 55 and 56 are independently arranged, and the second field stop 56 is detachably mounted on the first field stop 55. In this case, in the normal operation mode using the microscope 2, a circular visual field can be obtained by a circular field stop. When an image obtained by the hard endoscope 3 and displayed on the LCD monitor 26 and an image obtained by the surgical microscope 2 are to be simultaneously observed, a visual field free from the normal image circle 40 can be obtained by withdrawing the second field stop 56. Therefore, the degree of freedom increases in terms of the imaging position of the LCD monitor 26.

In addition, vignetting of an observation image obtained by the microscope 2 when endoscopic observation is also performed can be minimized, and a proper visual field can be obtained by shifting the imaging position of the LCD monitor 26 outside the visual field of the microscope 2 as far as possible within the performance of the eyepiece lens 7. Furthermore, this structure is simple, and hence can be realized at a low cost.

In this embodiment, the luminance of an optical image on the microscope 2 and the luminance of an image on the LCD monitor 26 are respectively detected by the first and second luminance sensors 54 and 60 to adjust the brightnesses of the lamp 62 and backlight 58 to an optimal light amount ratio. This allows the operator to always observe any observation images at optimal light amounts. In neurosurgical operations and the like, optical images on the microscope 2 are often observed in very bright conditions. If an image on the LCD monitor 26 is darker than an image on the microscope 2 in such a state, the light amount of the microscope 2 may be slightly reduced to make the operator easily observe the image on the LCD monitor 26. In contrast to this, when a red-reflex image or the like is to be observed in an operation in ophthalmology or the like, excessive brightness of an image on the LCD monitor 26 makes it difficult to see an optical image on the microscope 2. In this case, the two images can be easily observed by decreasing the luminance of the backlight 58. Even if the backlight 58 or lamp 62 deteriorates, and the light amount decreases, an optimal light amount ratio can always be obtained.

In addition, in this embodiment, since light from one backlight 58 is split into two light beams by the right and left prisms 59 to be supplied to the LCD monitors 26 for the right and left eyes, only one circuit for lighting the backlight 58 is required, an inexpensive arrangement can be realized. In addition, since the prisms 59 pivot in accordance with the eye distance even if the two LCD monitors 26 simultaneously move for eye distance adjustment, the backlight 58 need not move. This increases the degree of freedom in terms of observation and can prevent a wiring deterioration due to pivoting movement.

Furthermore, in this embodiment, the observation position of the hard endoscope 3 is detected by the navigation system, and a light-attenuating portion 75 for attenuating illumination light on the microscope 2 at this position is formed. This can prevent the light source for the microscope 2 from further illuminating a region illuminated by the hard endoscope 3. Assume that a halogen light source is used as a light source on the hard endoscope 3 side, and a xenon light source is used as a light source for the microscope 2 side. In this case, since illumination light from the xenon light source does not reach the region observed with the endoscope, endoscopic observation using the hard endoscope 3 can always be performed with a good color balance as long as white balance is ensured for the hard endoscope 3 alone. Assume that the distal end position of the hard endoscope 3 is detected by the navigation system, and the light-attenuating portion 75 for attenuating illumination light on the microscope 2 is formed at this portion. In this case, even if the distal end of the hard endoscope 3 shifts from a blind spot of the microscope 2, the illumination light incident on the hard endoscope 3 decreases in amount, and a halation or the like can be prevented. Therefore, a good endoscopic image can be obtained by the hard endoscope 3. This embodiment has the light-attenuating portion 75 for attenuating the light amount at the observation position or distal end position of the hard endoscope 3. Obviously, however, the same effect can be obtained by completely shielding light at this portion.

FIGS. 12 to 16C show the third embodiment of the present invention. FIG. 12 shows the overall arrangement of a surgical microscope and an endoscope. Referring to FIG. 12, reference numeral 101 denotes a microscope portion; 102, an objective lens common to right and left optical paths; 103, a zoom lens body having a pair of right and left magnification optical systems; and 104, an eyepiece barrel. The zoom lens body 103 incorporates an illumination optical system for irradiating a region with light from a light source and a light guide (none of which are shown). Referring to FIG. 12, reference numeral 105 denotes a frame portion for three-dimensionally supporting the microscope portion 101; 106, an endoscope; 107, a TV camera for shooting the observation image obtained by the endoscope 106; and 108, a CCU for the TV camera 107.

The arrangement of the eyepiece barrel 104 will be described next with reference to FIGS. 13 to 15. Note that since the right and left optical paths have the same arrangement, only one optical path will be described.

The eyepiece barrel 104 is optically coupled to the zoom lens body 103. More specifically, in the eyepiece barrel 104, an imaging lens 109, a mirror 110, an image rotator 111, a deflecting prism 112, and an eyepiece lens 114 are sequentially arranged from the zoom lens body 103 side. Reference numeral 115 denotes an eyepiece lens frame for holding the eyepiece lens 114.

The prism 113 is supported to be movable in a direction A indicated by the dotted line indicated by the dotted line in FIG. 13. The eyepiece lens 114 is supported to be movable in a direction B indicated by the dotted line in FIG. 13 upon movement of the prism 113. Reference numeral 121 denotes an image optical system holding frame supported by the eyepiece lens frame 115 to be pivotal about the optical axis of the eyepiece lens 114.

As shown in detail in FIGS. 14 and 15, the image optical system holding frame 121 has an image optical system (image projection optical system), i.e., a monitor 120, a lens 119, a mirror 118, and a projection prism 117 which are sequentially arranged. An exit surface 124 of the projection prism 117 is substantially flush with an imaging plane 116 of the microscope optical system. A reflecting surface 125 of the projection prism 117 is mirror-coated.

The image optical system holding frame 121 can be positioned with respect to the eyepiece lens frame 115 at 90°-intervals by a known clicking mechanism. Referring to FIG. 14, reference numeral 122 denotes a sensor for detecting the angular state of the image optical system holding frame 121; and 123, a video mixer having a known image rotating function. The video mixer 123 receives a video signal from the CCU 108 and outputs the video signal to the monitor 120. In addition, the signal obtained by the sensor 122 is input to the video mixer 123.

The function of the surgical microscope having the above arrangement will be described next.

Illumination light from a light source and a light guide (none of which are shown) is applied to a region by the illumination optical system incorporated in the zoom lens body 103 through the objective lens 102. The light reflected by the region passes through the objective lens 102 and the magnification optical system in the zoom lens body 103 to become an afocal light beam, and strikes the eyepiece barrel 104. The light incident on the eyepiece barrel 104 sequentially passes through the mirror 110, the image rotator 111, the deflecting prism 112, and the prism 113 and is formed into an image on the imaging plane 116 by the imaging lens 109. The image on the imaging plane 116 is observed under magnification with the eyepiece lens 114.

Eye distance adjustment in the eyepiece barrel 104 will be described below. When the prism 113 slides in the direction A, the eyepiece lens 114 moves in the direction B, thereby canceling the change in optical path length upon sliding of the prism 113. In this embodiment, eye distance adjustment is performed by a known Jentzsche scheme.

Figure 16A:
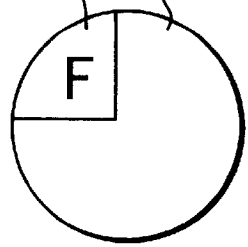
FIGS. 16A, 16B, and 16C are views each showing the observation state of the surgical microscope in FIG. 13.

The image obtained by the endoscope 106 is converted into a video signal by the TV camera 107 and the CCU 108 and displayed on the monitor 120 through the video mixer 123. The image light from the monitor 120 is formed into an image on the imaging plane 116 by the lens 119 through the mirror 118 and the projection prism 117. FIG. 16A shows the observation image on the eyepiece lens 114 at this time. As shown in FIG. 16A, the microscopic image formed on the imaging plane 116 by the imaging lens 109 is shielded by the mirror coat applied to the reflecting surface 125 of the projection prism 117. The image light from the monitor 120 is formed into an image on the imaging plane 116 flush with the microscopic image by the projection prism 117. The operator can therefore simultaneously observe the microscopic image and the monitor image. In this case, since the exit surface 124 of the projection prism 117 is substantially flush with the imaging plane 116, the exit surface 124 of the projection prism 117 itself serves as the boundary between the microscopic image and the monitor image.

Figure 16B:
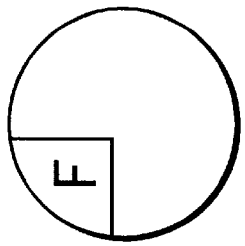
Figure 16C:
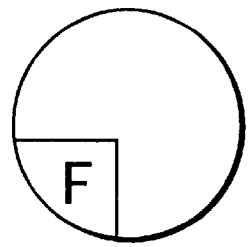
Figure 17:
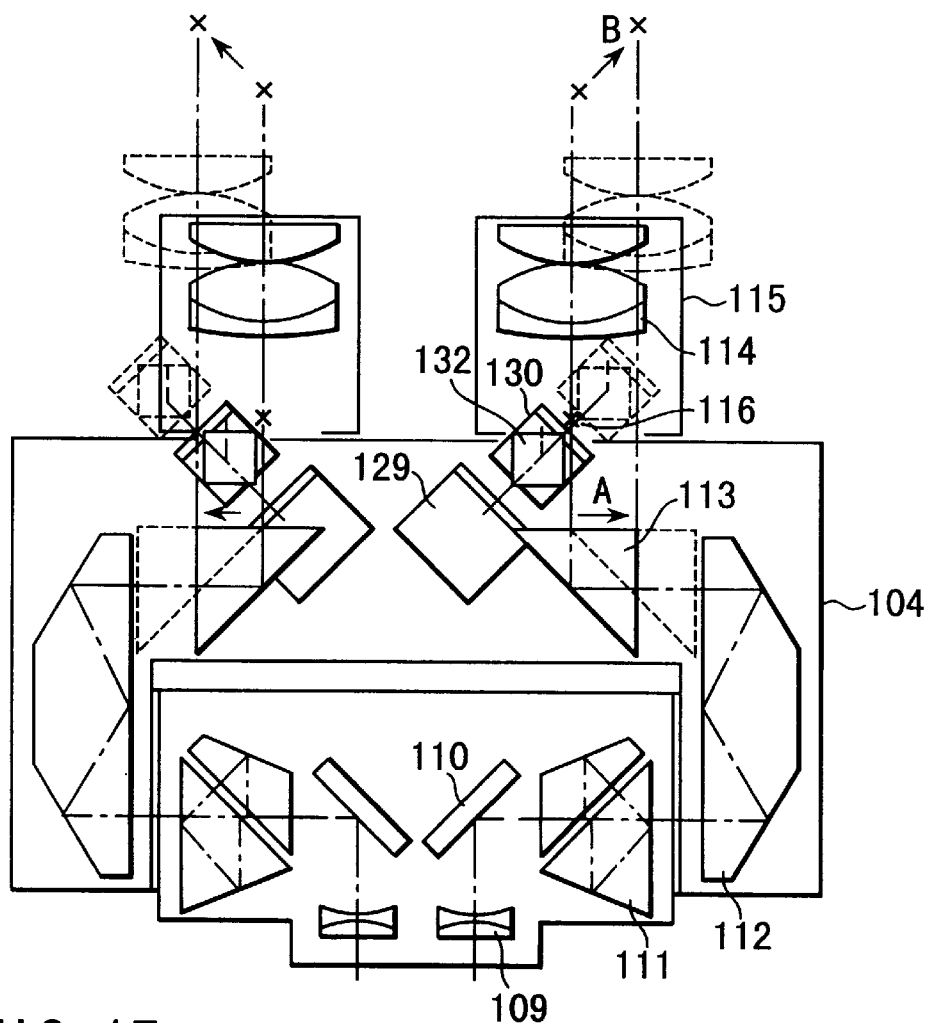
FIG. 17 is a front view of the eyepiece lens barrel of a surgical microscope according to the fourth embodiment of the present invention.
Figure 18:
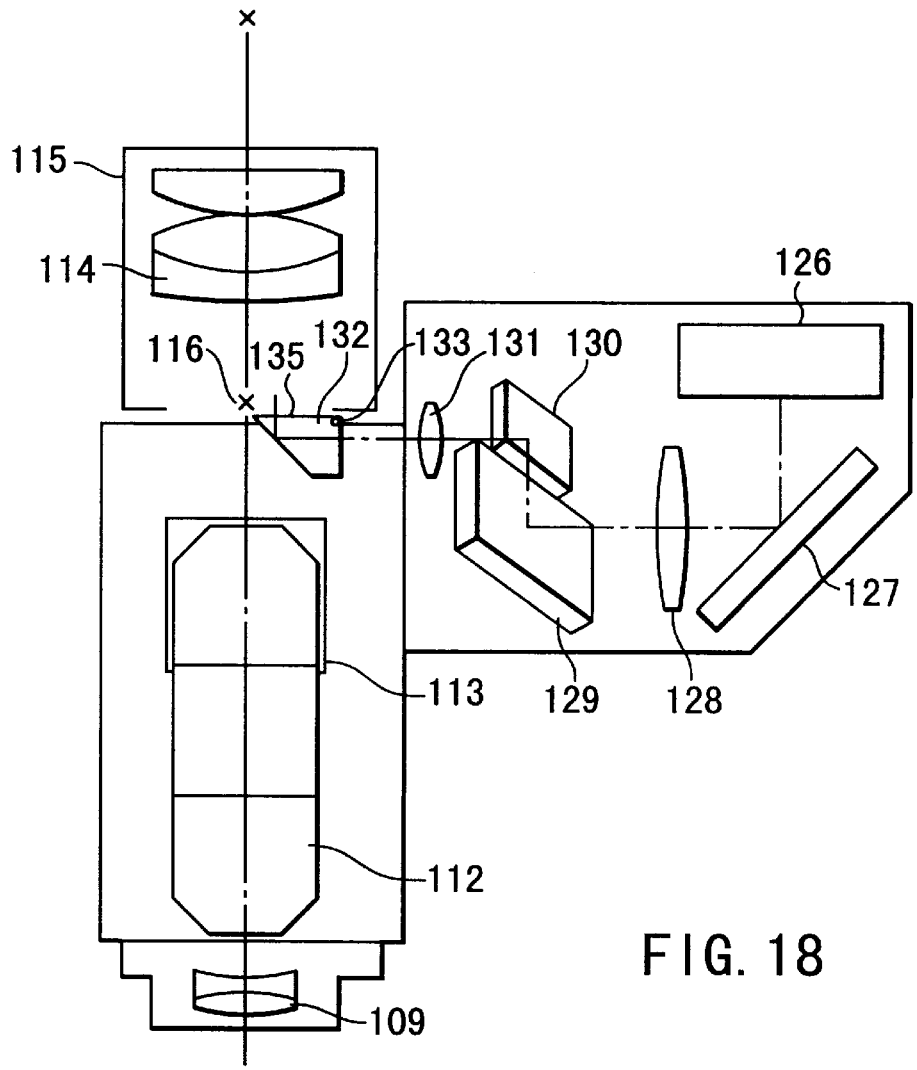
FIG. 18 is a side view showing the eyepiece lens barrel of the surgical microscope in FIG. 17.
Figure 19:
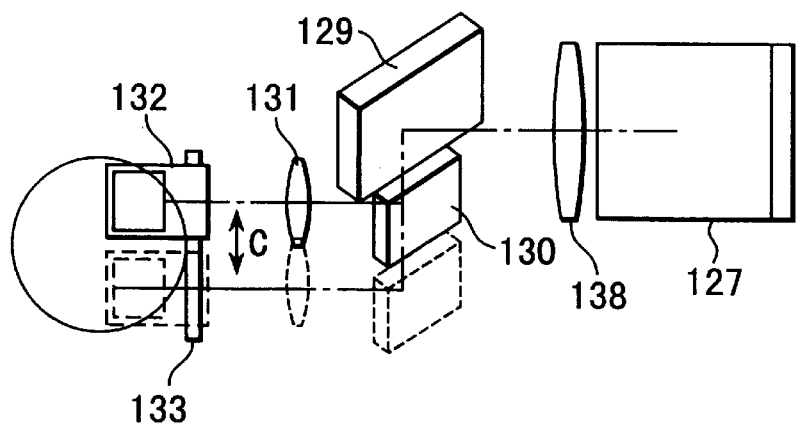
FIG. 19 is a plan view of the image optical system of the surgical microscope in FIG. 17.

In this embodiment, the position of the monitor image can be changed by rotating the image optical system holding frame 121. FIG. 16B shows the observation image obtained by rotating the image optical system holding frame 121 through 90° counterclockwise from the state shown in FIG. 16A. When the image optical system holding frame 121 is rotated, the rotation of the image optical system holding frame 121 is detected by the sensor 122, and the resultant signal is sent to the video mixer 123. The video mixer 123 always keeps the monitor image in a predetermined direction by correcting the rotation of the monitor image on the basis of the signal from the sensor 122, as shown in FIG. 16C.

As described above, according to the surgical microscope of this embodiment, since the position of the monitor image projected on a portion of the visual field of the microscope can be moved within the visual field of the microscope, the monitor image can be placed at a position where microscopic observation is not interfered. In addition, since the boundary between the microscopic image and the monitor image can be clearly observed, each image can be reliably recognized.

Although the image optical system holding frame 121 is manually rotated in this embodiment, this frame may be rotated by using a stepping motor or the like. In this case, the operator can change the positions of right and left monitor images together to arbitrary positions without using his/her hands. In addition, since the rotation of the image optical system holding frame 121 can be detected by using a signal from the stepping motor, the sensor 122 becomes unnecessary.

If the arrangement of this embodiment is combined with that of the first or second embodiment, the functions and effects of the two embodiments can be obtained together. Assume that the projection prism 117 is detachably mounted on the microscope optical system as in the first or second embodiment, and the respective constituent elements of the microscope optical system, the illumination optical system, the image optical system (image projection optical system), the photographing optical system, and the control system have the same arrangements as those in the first or second embodiment while the arrangement of the main part of this embodiment is maintained. In this case, the functions and effects of the first or second embodiment can be obtained together with the functions and effect of this embodiment.

FIGS. 17 to 22C show the fourth embodiment of the present invention. Note that the same reference numerals in this embodiment denote the same parts as in the third embodiment, and a description thereof will be omitted.

Figure 20A:
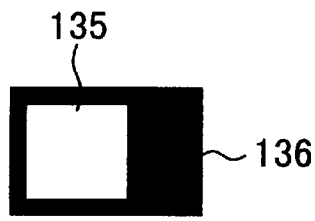
FIGS. 20A and 20B are views showing how the projection prism of the surgical microscope in FIG. 17 is coated.
Figure 20B:
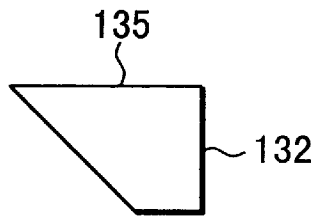
Figure 21:
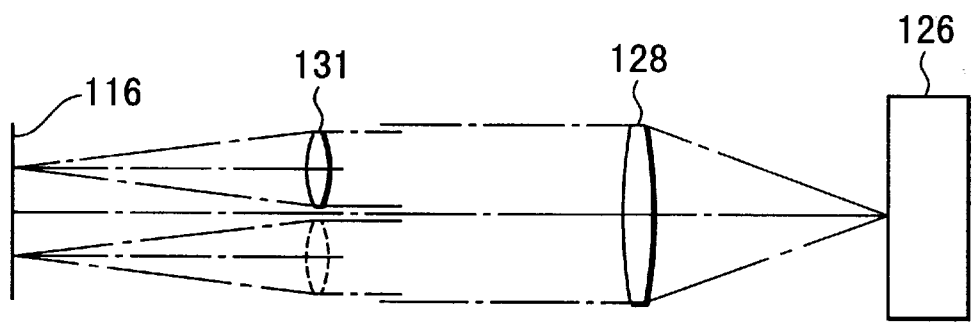
FIG. 21 is a view showing the optical principle of the image optical system of the surgical microscope in FIG. 17.

The arrangement of an image optical system will be described first with reference to FIGS. 17 to 20. Note that since the right and left optical path have the same arrangement, only one optical path will be described below. As shown in detail in FIG. 18, the image optical system comprises a monitor 126, a mirror 127, a lens 128, a mirror 129, a mirror 130, an imaging lens 131, and a projection prism 132. The direction of a light beam propagating from the mirror 129 to the mirror 130 is the same as the direction (direction B) in which an eyepiece lens 114 moves when eye distance adjustment is performed. The mirror 130, the imaging lens 131, and the projection prism 132 are supported by an eyepiece lens frame 115 to move together with the eyepiece lens 114 in eye distance adjustment. These optical elements 130, 131, and 132 can be moved along a shaft 133 in a direction C (parallel to an imaging plane 116) indicated by the dotted line in FIG. 19. An exit surface 135 of the projection prism 132 is substantially flush with the imaging plane 116. A field mask 136 is formed around the exit surface 135 by coating, as shown in FIG. 20.

The function of the surgical microscope having the above arrangement will be described next.

Figures 22A, 22B, 22C:
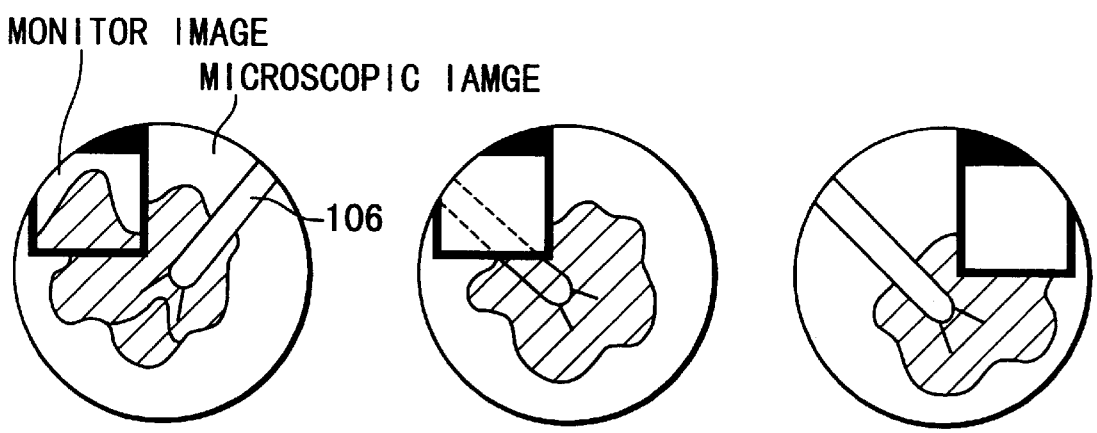
FIGS. 22A, 22B, and 22C are views each showing the observation state of the surgical microscope in FIG. 17.

Image light from the monitor 126 is reflected by the mirror 127 and converted into an afocal light beam by the lens 128. This light beam is reflected by the mirrors 129 and 130 and formed into an image on the imaging plane 116 by the imaging lens 131 through the projection prism 132. FIG. 22A shows the observation image obtained at this time. As shown in FIG. 22A, since the field mask 136 is formed on the exit surface 135 of the projection prism 132, the boundary between the microscopic image and the monitor image is displayed. In addition, as shown in FIG. 22B, when the endoscope 106 hides behind the monitor image, the projection prism 132, the imaging lens 131, and the mirror 130 may be moved along the shaft 133 to the positions indicated by the dotted lines in FIG. 19. With this operation, an observation image like the one shown in FIG. 22C can be obtained. The reason why such an observation image is obtained is based on the optical principle shown in FIG. 21. That is, since image light from the monitor 126 is converted into an afocal light beam by the lens 128, the image on the monitor 126 can be projected onto the imaging plane 116 as long as the imaging lens 131 moves within the afocal light beam.

As described above, according to the surgical microscope of this embodiment, substantially the same effects as those of the third embodiment can be obtained, and an microscopic image circle 104 can be reduced in size because the overall image optical system need not be moved when a monitor image is to be moved. Furthermore, since the boundary between a microscopic image and a monitor image is displayed, each image can be easily discriminated as compared with the third embodiment. This function is especially effective for projection of a 3-D image (projection of a 3-D image as a monitor image), in which the parallax between the right and left eyes makes it difficult to discriminate the boundary portion (the boundary portion between a microscopic image and a monitor image).

In this embodiment, a field mask is formed as a rectangular frame, but the same effect can be obtained with a circular field mask. If the arrangement of this embodiment is combined with that of the first or second embodiment, the functions and effects of the two embodiments can be obtained together. Assume that the projection prism 132 is detachably mounted on the microscope optical system as in the first or second embodiment, and the respective constituent elements of the microscope optical system, the illumination optical system, the image optical system (image projection optical system), the photographing optical system, and the control system have the same arrangements as those in the first or second embodiment while the arrangement of the main part of this embodiment is maintained. In this case, the functions and effects of the first or second embodiment can be obtained together with the functions and effect of this embodiment.

FIGS. 23 to 26A and 26B show the fifth embodiment of the present invention. Note that the same reference numerals in this embodiment denote the same parts as in the third and fourth embodiments, and a description thereof will be omitted.

The arrangement of this embodiment will be described first with reference to FIG. 23. A projection prism 132 and an imaging lens 131 are supported to be movable in a direction D (optical axis direction) indicated by the dotted line in FIG. 23. Reference numeral 138 denotes a sensor for detecting the movement amounts of the projection prism 132 and the imaging lens 131. A signal from the imaging lens 131 is input to a video mixer 139. The video mixer 139 has the function of changing the display range and magnification of an image. An endoscopic image and waveform information from a nerve monitor (not shown) are input to the video mixer 139. A video output signal from the video mixer 139 is transmitted to a monitor 126. The video transmitted to the monitor 126 is an endoscopic image or nerve monitor waveform. These video data can be selectively transmitted.

The function of the surgical microscope having the above arrangement will be described next.

Figure 23:
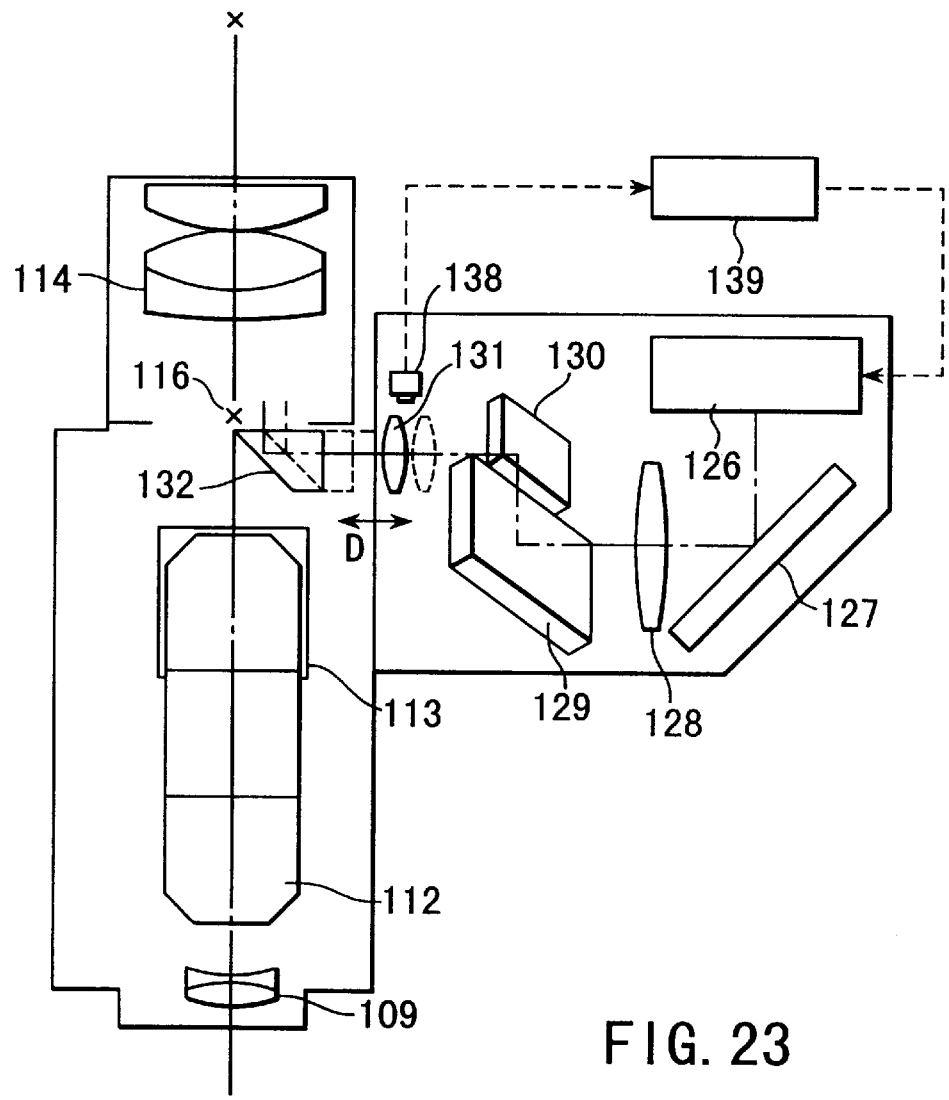
FIG. 23 is a side view of the eyepiece lens barrel of a surgical microscope according to the fifth embodiment of the present invention.
Figure 24:
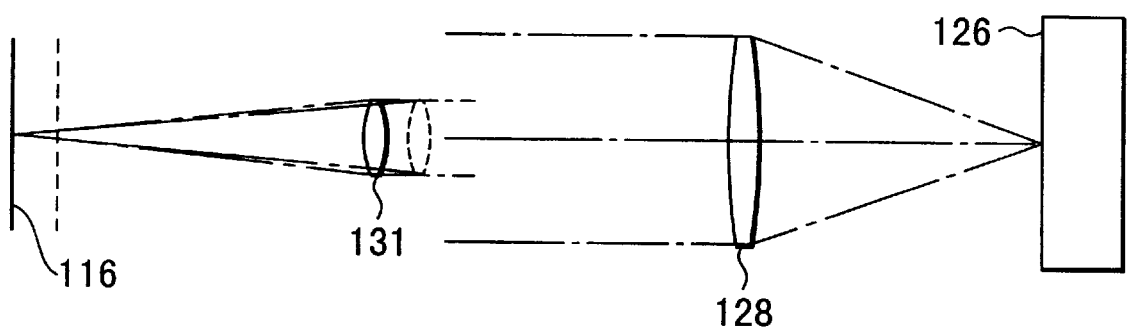
FIG. 24 is a view showing the optical principle of the image optical system of the surgical microscope in FIG. 23.
Figures 25A, 25B:
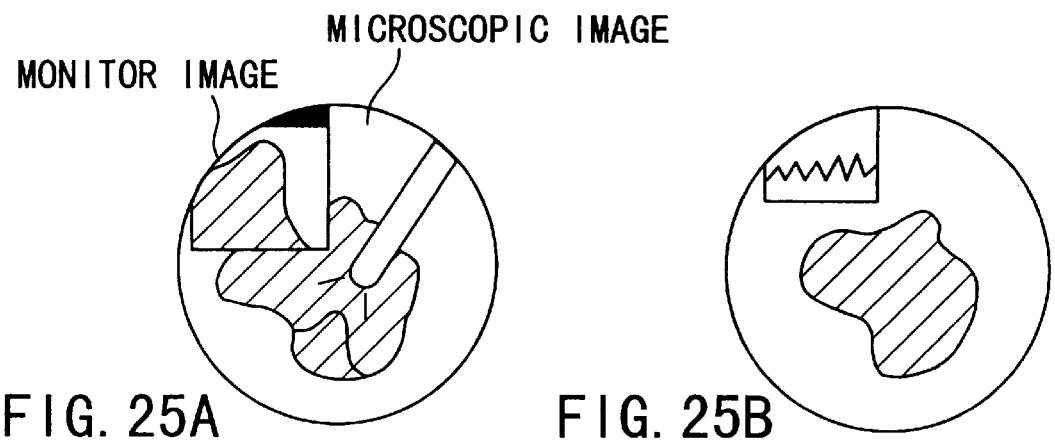
FIGS. 25A and 25B are views each showing the observation state of the surgical microscope in FIG. 23.
Figures 26A, 26B:
FIGS. 26A and 26B are views each showing the display range of a monitor.

FIG. 25A shows the observation image obtained when the projection prism 132 and the imaging lens 131 are located at the positions indicated by the solid lines in FIG. 23. At this time, an endoscopic image is selected as a video output signal from the video mixer 139, and the endoscopic image is displayed on the entire screen of the monitor 126, as shown in FIG. 26A. When waveforms from the nerve monitor are to be observed, the projection prism 132 and the imaging lens 131 are moved to the positions indicated by the dotted lines in FIG. 23. At this time, the movement of the projection prism 132 and imaging lens 131 is detected by the sensor 138, and the detection signal is sent from the sensor 138 to the video mixer 139. With this operation, video output signals from the video mixer 139 are switched, and the display range of the monitor 126 is reduced to the upper half, as shown in FIG. 26B. That is, the display ranges of the monitor 126 are switched in accordance with the range in which the projection prism 132 is observed by an eyepiece lens 114. FIG. 25B shows the observation image obtained at this time. FIG. 24 shows the optical principle in this case. More specifically, since image light from the monitor 126 is converted into an afocal light beam by a lens 128, even if the imaging lens 131 moves in the optical axis direction, the distance from the imaging lens 131 to an imaging plane 116 does not change. Even if, therefore, the optical path length of the image optical system changes, image light from the monitor 126 is formed into an image on the imaging plane 116.

As described above, according to the surgical microscope of this embodiment, since the size of the monitor image display range within the visual field of the microscope can be changed in accordance with the type of image to be projected on a monitor image, vignetting of the microscopic image can be minimized when no problem is posed even if the monitor image display range is small as in the case of a nerve monitor waveform. In addition, since the size of the monitor image display range can be changed without moving the entire image optical system, a microscopic image circle 104 can be reduced in size.

If the arrangement of this embodiment is combined with that of the first or second embodiment, the functions and effects of the two embodiments can be obtained together. Assume that the projection prism 132 is detachably mounted on the microscope optical system as in the first or second embodiment, and the respective constituent elements of the microscope optical system, the illumination optical system, the image optical system (image projection optical system), the photographing optical system, and the control system have the same arrangements as those in the first or second embodiment while the arrangement of the main part of this embodiment is maintained. In this case, the functions and effects of the first or second embodiment can be obtained together with the functions and effect of this embodiment.

Figure 27:
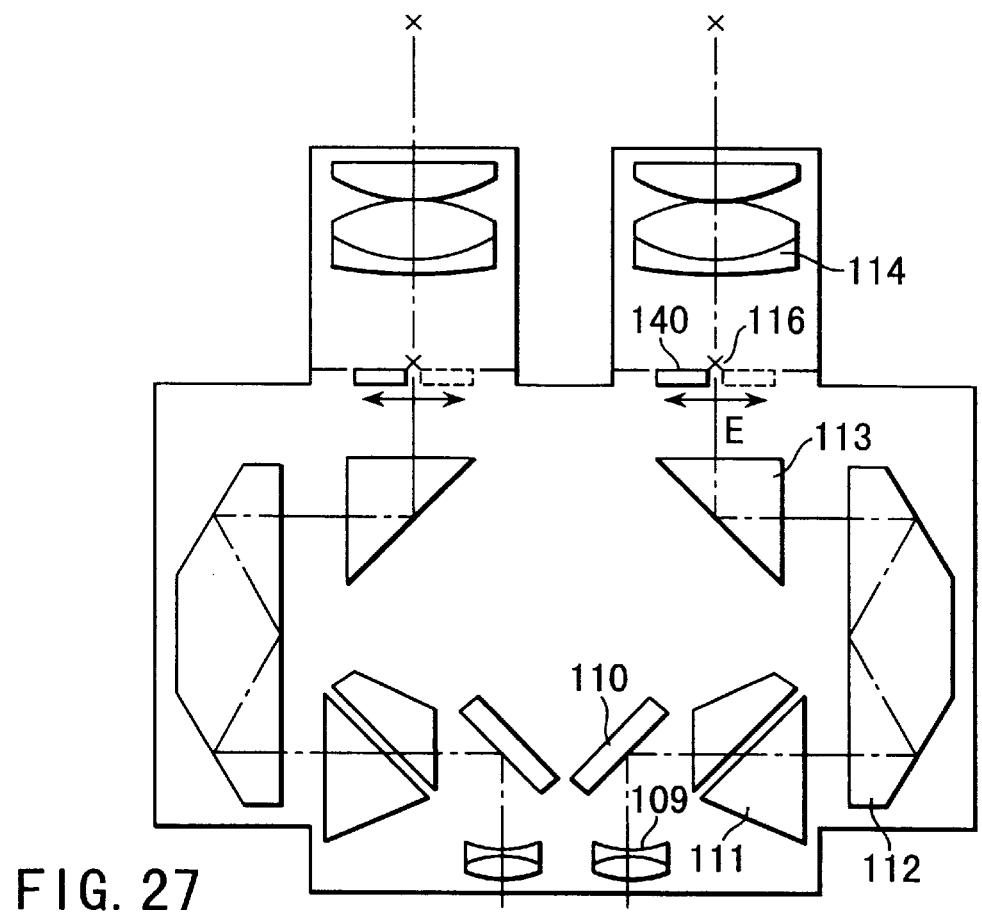
FIG. 27 is a front view of the eyepiece lens barrel of a surgical microscope according to the sixth embodiment of the present invention.

FIGS. 27 and 28 show the sixth embodiment of the present invention. Note that the same reference numerals in this embodiment denote the same parts as in the third to fifth embodiments, and a description thereof will be omitted.

As shown in FIGS. 27 and 28, a surgical microscope according to this embodiment has a liquid crystal monitor 140. The liquid crystal monitor 140 is placed at almost the same position as that of an imaging plane 116, and is supported to be movable in the horizontal direction (direction E indicated by the arrow in FIG. 27) and the vertical direction (F direction indicated by the arrow in FIG. 28) within a plane parallel to the imaging plane 116.

The function of the surgical microscope having the above arrangement will be described next.

The observation image obtained when the liquid crystal monitor 140 is placed at the position indicated by the solid line in FIG. 27 is the same as that shown in FIG. 22A. More specifically, a portion of the microscopic image is shielded by the liquid crystal monitor 140. Obviously, the microscopic image and the monitor image can be simultaneously observed because the liquid crystal monitor 140 is substantially flush with the imaging plane 116. When the liquid crystal monitor 140 is moved to the position indicated by the dotted line in FIG. 27, the observation image becomes the same as that shown in FIG. 22C. The observation image obtained when the liquid crystal monitor 140 is located at the position indicated by the solid line in FIG. 28 is the same as that shown in FIG. 25A. When the liquid crystal monitor 140 is moved from this solid line position to the dotted line position, an observation image like the one shown in FIG. 25B can be obtained.

As described above, according to the surgical microscope of this embodiment, almost the same effects as those of the fourth and fifth embodiments can be obtained. In addition, since the position and size of a monitor image (display) within the visual field of the microscope can be changed by only moving the liquid crystal monitor 140 alone, the size of the apparatus can be reduced.

If the arrangement of this embodiment is combined with that of the first or second embodiment, the functions and effects of the two embodiments can be obtained together. Assume that the liquid crystal monitor 140 is detachably mounted on the microscope optical system as in the first or second embodiment, and the respective constituent elements of the microscope optical system, the illumination optical system, the image optical system (image projection optical system), the photographing optical system, and the control system have the same arrangements as those in the first or second embodiment while the arrangement of the main part of this embodiment is maintained. In this case, the functions and effects of the first or second embodiment can be obtained together with the functions and effect of this embodiment.

FIGS. 29, 30A, and 30B show the seventh embodiment of the present invention. Note that the same reference numerals in this embodiment denote the same parts as in the sixth embodiment, and a description thereof will be omitted.

As shown in FIG. 29, a surgical microscope according to this embodiment has a liquid crystal monitor 143. This liquid crystal monitor 143 is located at almost the same position as that of an imaging plane 116, and is supported to be pivotal about a rotating shaft 144 in a direction G indicated by the arrow.

FIG. 30A shows the observation image obtained when the liquid crystal monitor 143 is located at the position indicated by the solid line in FIG. 29. As shown in FIG. 29, character information is projected on the liquid crystal monitor 143. When the liquid crystal monitor 143 is moved from this solid line position to the dotted line position, an observation image like the one shown in FIG. 30B can be obtained.

As described above, according to the surgical microscope of this embodiment, since the size of a monitor image within the visual field of the microscope can be changed by rotating/moving the liquid crystal monitor 143, when no problem is posed in oblique observation of the liquid crystal monitor 143 as in the case of character information, the arrangement can be simplified, thus providing a lightweight, inexpensive apparatus.

In this embodiment, the liquid crystal monitor 143 is observed obliquely, a detection means for detecting the rotation amount of the liquid crystal monitor 143 may be used to correct the display of the liquid crystal monitor 143 on the basis of the information from the detection means, as shown in FIGS. 31A and 31B.

If the arrangement of this embodiment is combined with that of the first or second embodiment, the functions and effects of the two embodiments can be obtained together. Assume that the liquid crystal monitor 143 is detachably mounted on the microscope optical system as in the first or second embodiment, and the respective constituent elements of the microscope optical system, the illumination optical system, the image optical system (image projection optical system), the photographing optical system, and the control system have the same arrangements as those in the first or second embodiment while the arrangement of the main part of this embodiment is maintained. In this case, the functions and effects of the first or second embodiment can be obtained together with the functions and effect of this embodiment.

Figure 32:
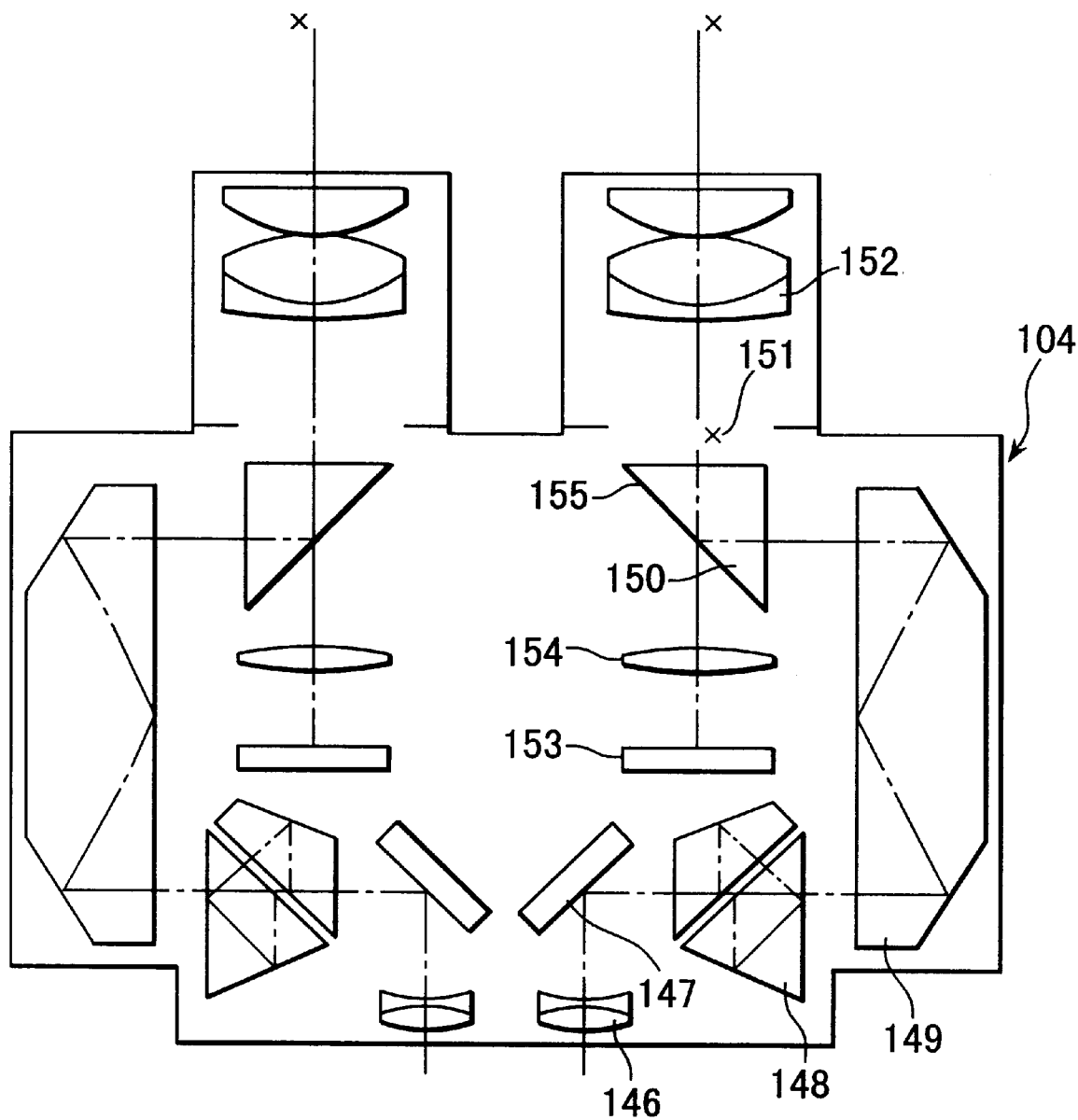
FIG. 32 is a front view of the eyepiece lens barrel of a surgical microscope according to the eighth embodiment of the present invention.
Figure 33:
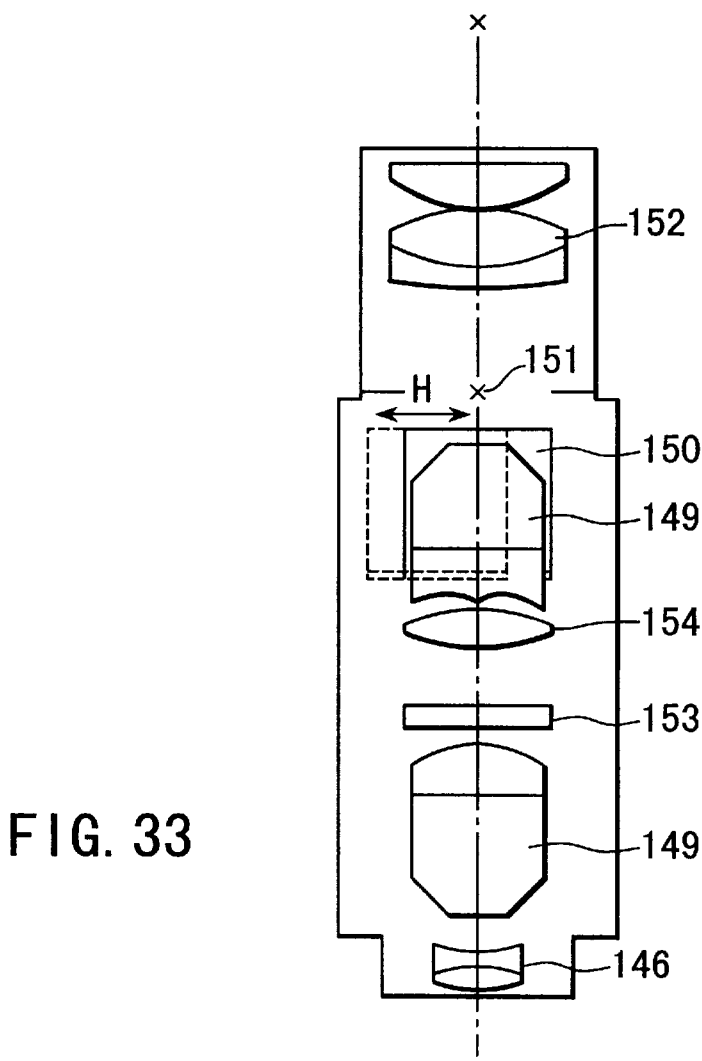
FIG. 33 is a side view of the eyepiece lens barrel in FIG. 32.

FIGS. 32 to 34C show the eighth embodiment of the present invention. As shown in FIGS. 32 and 33, an eyepiece lens barrel 104 optically coupled to a zoom lens body has a pair of right and left optical paths as in the third embodiment. Note that since the right and left optical paths have the same arrangement, only one optical path will be described below.

In the eyepiece lens barrel 104, an imaging lens 146, a mirror 147, an image rotator 148, a deflecting prism 149, a prism 150, and an eyepiece lens 152 are sequentially arranged from the light-transmitting portion 103 side. A reflecting surface 155 of the prism 150 is mirror-coated. The prism 150 is supported to be movable in a direction H indicated by the arrow in FIG. 33. A projection lens 154 and a liquid crystal monitor 153 are arranged on the extended line of the optical axis of the eyepiece lens 152. In this case, the projection lens 154 is located to form image light from the liquid crystal monitor 153 into an image on an imaging plane 151.

The function of the surgical microscope having the above arrangement will be described next.

Figure 34A:
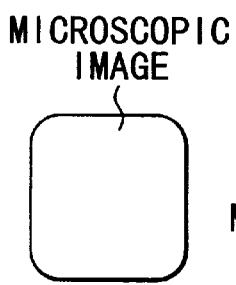
FIGS. 34A, 34B, and 34C are views each showing the observation state of the surgical microscope in FIG. 32.
Figure 34B:
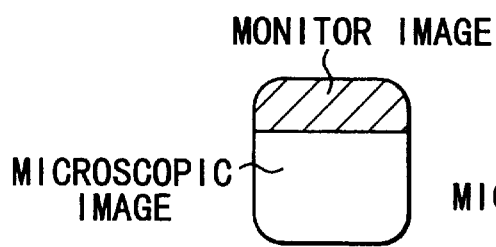
Figure 34C:
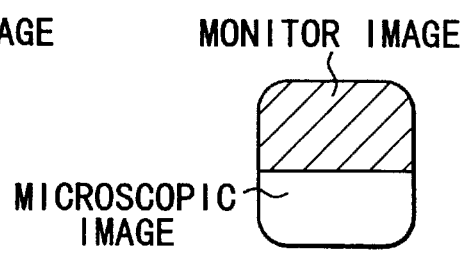

A light beam from the zoom lens body (not shown) is formed into an image on the imaging plane 151 by the imaging lens 146 upon sequentially passing through the mirror 147, the image rotator 148, the deflecting prism 149, and the prism 150. The image on the imaging plane 151 is observed under magnification with the eyepiece lens 152. In this case, when the prism 150 is located at the solid line position in FIG. 33, a light beam from the liquid crystal monitor 153 is shielded by the mirror coat on the reflecting surface 155 of the prism 150 and hence does not reach the imaging plane 151. FIG. 34A shows the observation image obtained at this time. When the prism 150 is moved to the dotted line position in FIG. 33, part of the light beam from the liquid crystal monitor 153 is formed into an image on the imaging plane 151. FIG. 34B shows the observation image obtained at this time. When the prism 150 is further moved in this state, an observation image like the one shown in FIG. 34C can be obtained. When the prism 150 completely retreats from the microscope optical path, only a monitor image is observed as an observation image.

As described above, according to the surgical microscope of this embodiment, the projection ratio between a microscopic image and a monitor image within the visual field of the microscope can be arbitrarily changed.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A surgical microscope comprising:
   an illumination optical system for illuminating a microscope visual field;
   an observation optical system which has an eyepiece lens and an imaging lens and allows observation of a first image of an observation target by guiding reflected light to the eyepiece lens from the observation target irradiated with illumination light from said illumination optical system;
   an image projection optical system for projecting a second image as image information within a portion of the microscope visual field; and
   projection position changing means for changing a projection position of the second image with respect to the microscope visual field.

2. A microscope according to claim 1, wherein said image projection optical system comprises a light guide member which is inserted in an optical path of said observation optical system and guides light forming the second image toward an image plane of the imaging lens, and
   said projection position changing means moves said light guide member within the optical path of said observation optical system.

3. A microscope according to claim 2, wherein said light guide member is a prism.

4. A microscope according to claim 2, wherein said light guide member moves parallel with an image plane of the imaging lens.

5. A microscope according to claim 2, wherein said light guide member rotates about an optical axis of said observation optical system.

6. A microscope according to claim 2, further comprising field stop means, placed at substantially the same position as the imaging position of the imaging lens, for bordering the first and second images.

7. A microscope according to claim 2, wherein a light exit surface of said light guide member is placed at substantially the same position as the imaging position of the imaging lens.

8. A microscope according to claim 7, wherein stop field means for bordering the first and second images is formed on the light exit surface of said light guide member.

9. A microscope according to claim 8, wherein said field stop means is a field mask formed on the light exit surface of said light guide member by coating.

10. A microscope according to claim 1, wherein said image projection optical system comprises a monitor inserted in the optical path of said observation optical system, and said projection position changing means moves said monitor within the optical path of said observation optical system.

11. A microscope according to claim 10, wherein said monitor is a liquid crystal monitor.

12. A microscope according to claim 10, wherein said monitor moves parallel with the imaging plane of the imaging lens.

13. A microscope according to claim 10, wherein said monitor rotates about an axis parallel to the imaging plane of the imaging lens.

14. A microscope according to claim 2, wherein said image projection optical system comprises a relay optical system for converting the light forming the second image into an afocal light beam and a projection optical system for forming the afocal light beam into an image on the imaging plane of the imaging lens, and said projection position changing means moves said projection optical system within the afocal light beam emerging from said relay optical system such that said light guide member moves within the optical path of said observation optical system.

15. A microscope according td claim 14, wherein said projection optical system moves in a direction perpendicular to an optical axis of the afocal light beam.

16. A microscope according to claim 14, wherein said projection optical system moves in a direction parallel to an optical axis of the afocal light beam.

17. A microscope according to claim 1, wherein said observation optical system comprises a reflecting member for reflecting the light forming the first image and guiding the light to the imaging position of the imaging lens, said reflecting member is placed between the imaging position of the imaging lens and said image projection optical system, and said projection position changing means moves said reflecting member in a direction parallel with respect to the imaging plane of the imaging lens.

18. A microscope according to claim 14, wherein said image projection optical system comprises a display for displaying the second image, and further comprising detection means for detecting movement of said projection optical system, and control means for changing a display state of the second image on said display on the basis of a detection result obtained by said detection means.

19. A microscope according to claim 1, wherein said observation optical system comprises a right eye observation optical system and left eye observation optical system corresponding to right and left eyes, said image projection optical system comprises a right eye image projection optical system for projecting the second image within a microscope visual field formed by said right eye observation optical system and a left eye image projection optical system for projecting the second image within a microscope visual field formed by said left eye observation optical system, said projection position changing means comprises first means for changing a projection position of the second image projected within a microscope visual field formed by said right eye observation optical system through said right eye image projection optical system, and second means for changing a projection position of the second image projected within a microscope visual field formed by said left eye observation optical system through said left eye image projection optical system, and said right and left eye observation optical systems and said right and left eye image projection optical systems are interlocked with each other.

* * * * *